United States Patent
Das et al.

(10) Patent No.: US 12,272,023 B2
(45) Date of Patent: Apr. 8, 2025

(54) DEEP LEARNING MULTI-PLANAR REFORMATTING OF MEDICAL IMAGES

(71) Applicant: GE Precision Healthcare LLC, Wauwatosa, WI (US)

(72) Inventors: Bipul Das, Chennai (IN); Rakesh Mullick, Bangalore (IN); Deepa Anand, Bangalore (IN); Sandeep Dutta, Celebration, FL (US); Uday Damodar Patil, Bangalore (IN); Maud Bonnard, Brookfield, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 399 days.

(21) Appl. No.: 17/654,864

(22) Filed: Mar. 15, 2022

(65) Prior Publication Data
US 2023/0298136 A1 Sep. 21, 2023

(51) Int. Cl.
*G06T 3/60* (2024.01)
*G06T 7/73* (2017.01)
(Continued)

(52) U.S. Cl.
CPC .......... *G06T 3/60* (2013.01); *G06T 7/73* (2017.01); *G06V 10/774* (2022.01); *G06V 10/82* (2022.01);
(Continued)

(58) Field of Classification Search
CPC ... G06T 7/73; G06T 3/60; G06T 2207/20084; G06T 2207/20081; G06T 2200/04;
(Continued)

(56) References Cited

U.S. PATENT DOCUMENTS

| 990,712 A | 4/1911 | Deiterich et al. |
| 7,636,463 B2 | 12/2009 | Deshapande et al. |

(Continued)

FOREIGN PATENT DOCUMENTS

| EP | 3855396 A2 | 7/2021 |
| WO | 2021082629 A1 | 5/2021 |

OTHER PUBLICATIONS

Nishimoto, S. et al. | "Three-dimensional cranio-facial landmark detection in CT slices from a publicly available database, using multi-phased regression networks on a personal computer". medRxiv preprint doi: https://doi.org/10.1101/2021.03.21.21253999; this version posted Mar. 26, 2021, 7 pages.
(Continued)

*Primary Examiner* — Tuan H Nguyen

(57) ABSTRACT

Systems/techniques that facilitate deep learning multi-planar reformatting of medical images are provided. In various embodiments, a system can access a three-dimensional medical image. In various aspects, the system can localize, via execution of a machine learning model, a set of landmarks depicted in the three-dimensional medical image, a set of principal anatomical planes depicted in the three-dimensional medical image, and a set of organs depicted in the three-dimensional medical image. In various instances, the system can determine an anatomical orientation exhibited by the three-dimensional medical image, based on the set of landmarks, the set of principal anatomical planes, or the set of organs. In various cases, the system can rotate the three-dimensional medical image, such that the anatomical orientation now matches a predetermined anatomical orientation.

16 Claims, 15 Drawing Sheets

(51) Int. Cl.
*G06V 10/774* (2022.01)
*G06V 10/82* (2022.01)
*G16H 50/20* (2018.01)

(52) U.S. Cl.
CPC ......... *G16H 50/20* (2018.01); *G06T 2200/04* (2013.01); *G06T 2207/20081* (2013.01); *G06T 2207/20084* (2013.01); *G06V 2201/031* (2022.01)

(58) Field of Classification Search
CPC .. G16H 50/20; G16H 2201/031; G06V 10/82; G06V 10/774
See application file for complete search history.

(56) References Cited

U.S. PATENT DOCUMENTS

| | | | |
|---|---|---|---|
| 7,822,254 | B2 | 10/2010 | Yatziv et al. |
| 9,113,781 | B2 * | 8/2015 | Wels ............... A61B 5/0036 |
| 9,208,582 | B2 | 12/2015 | Omi et al. |
| 10,354,555 | B2 * | 7/2019 | Thaler ............... G09B 23/28 |
| 11,182,896 | B2 | 11/2021 | Avendi et al. |

OTHER PUBLICATIONS

Yeh, Y.-Ch. et al | "Deep learning approach for automatic landmark detection and alignment analysis in whole-spine lateral radiographs". Sci Rep. Apr. 7, 2021;11(1):7618. doi: 10.1038/s41598-021-87141-x, 15 pages.

Nunez-Garcia, M. et al. | "Automatic multiplanar CT reformatting from trans-axial into left ventricle short-axis view". HAL Id: hal-02961500, https://hal.inria.fr/hal-02961500, Submitted on Oct. 8, 2020, 11 pages.

Zhong, Zh. et al. | "An Attention-Guided Deep Regression Model for Landmark Detection in Cephalograms". arXiv:1906.07549 [eess.IV], 10.1007/978-3-030-32226-7_60, Submitted Jun. 17, 2019, 9 pages.

Grewal, M. et al. | "An End-to-end Deep Learning Approach for Landmark Detection and Matching in Medical Images". arXiv:2001.07434v1 [cs.CV] Jan. 21, 2020, 10 pages.

O'Neil, A. Q. et al. | "Attaining human-level performance with atlas location autocontext for anatomical landmark detection in 3D CT data". arXiv:1805.08687v2 [cs.CV] Sep. 30, 2018, 15 pages.

Deshpande, H. et al. | "Deep learning for the detection of landmarks in head CT images and automatic quality assessment". 16. 10.1117/12.2581810 (2011), 9 pages.

* cited by examiner

DEEP LEARNING MULTI-PLANAR REFORMATTING OF MEDICAL IMAGES

TECHNICAL FIELD

The subject disclosure relates generally to multi-planar reformatting, and more specifically to deep learning multi-planar reformatting of medical images.

BACKGROUND

Multi-planar reformatting involves rotating a given medical image volume such that the given medical image volume exhibits a desired orientation. Some potential techniques for facilitating multi-planar reformatting are manually performed by medical professionals. Such potential techniques are time-consuming, non-reproducible, and prone to human error. Other potential techniques attempt to address the shortcomings of manual multi-planar reformatting by utilizing deep learning. However, such other potential techniques often suffer from insufficiently high accuracy and/or precision.

Accordingly, systems and/or techniques that can address one or more of these technical problems can be desirable.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate deep learning multi-planar reformatting of medical images are described.

According to one or more embodiments, a system is provided. The system can comprise a computer-readable memory that can store computer-executable components. The system can further comprise a processor that can be operably coupled to the computer-readable memory and that can execute the computer-executable components stored in the computer-readable memory. In various embodiments, the computer-executable components can comprise a receiver component. In various aspects, the receiver component can access a three-dimensional medical image. In various embodiments, the computer-executable components can further comprise a detection component. In various cases, the detection component can localize, via execution of a machine learning model, a set of landmarks depicted in the three-dimensional medical image, a set of principal anatomical planes depicted in the three-dimensional medical image, and/or a set of organs depicted in the three-dimensional medical image. In various instances, the computer-executable components can further comprise an orientation component. In various cases, the orientation component can determine an anatomical orientation exhibited by the three-dimensional medical image, based on the set of landmarks, the set of principal anatomical planes, and/or the set of organs. In various aspects, the computer-executable components can further comprise an execution component. In various cases, the execution component can rotate the three-dimensional medical image, such that the anatomical orientation now matches a predetermined anatomical orientation.

According to one or more embodiments, the above-described system can be implemented as a computer-implemented method and/or a computer program product.

DETAILED DESCRIPTION

Figure 1:
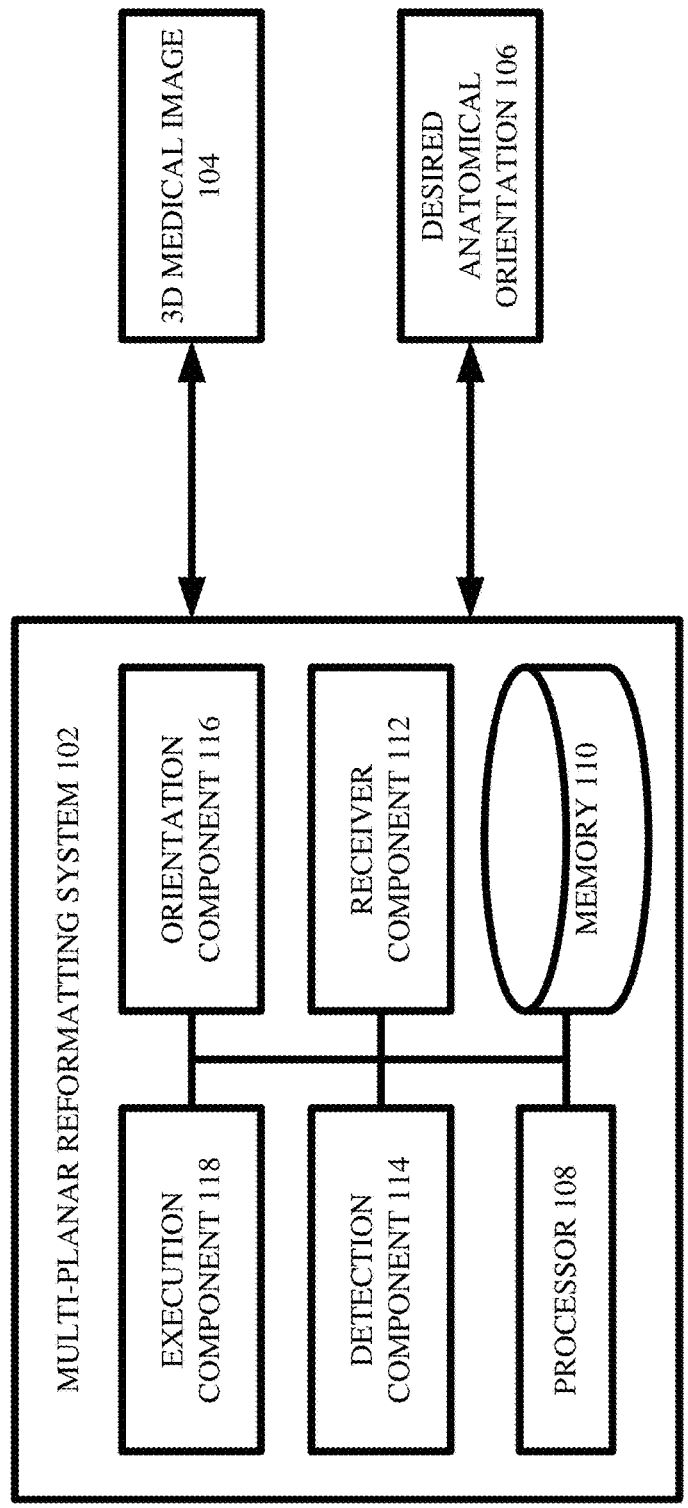
FIG. 1 illustrates a block diagram of an example, non-limiting system that facilitates deep learning multi-planar reformatting for medical images in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Multi-planar reformatting can involve rotating and/or translating a given medical image volume (e.g., a computed tomography (CT) voxel array, a magnetic resonance imaging (MRI) voxel array, an X-ray voxel array, a positron emission tomography (PET) voxel array, an ultrasound voxel array) such that the given medical image volume exhibits a desired orientation (e.g., such that an anatomical structure depicted in the given medical image volume is displayed and/or positioned according to the desired orientation).

Some potential techniques for facilitating multi-planar reformatting are manually performed by medical professionals. That is, a medical professional manually manipulates a medical image volume until the medical image volume exhibits the desired orientation. Unfortunately, such potential techniques are time-consuming, non-reproducible, and prone to human error.

Other potential techniques attempt to address the shortcomings of manual multi-planar reformatting by utilizing deep learning. That is, such other potential techniques involve training a deep learning model to automatically perform multi-planar reformatting on an inputted medical image volume. However, such other potential techniques often suffer from insufficiently high accuracy and/or precision.

Accordingly, systems and/or techniques that can address one or more of these technical problems can be desirable.

Various embodiments of the subject innovation can address one or more of these technical problems. One or more embodiments described herein include systems, computer-implemented methods, apparatus, and/or computer program products that can facilitate deep learning multi-planar reformatting of medical images. More specifically, various embodiments described herein can be considered as a computerized tool (e.g., any suitable combination of computer-executable hardware and/or computer-executable software) that can receive as input a medical image volume and that can utilize machine learning (e.g., a deep learning neural network) to facilitate and/or perform multi-planar reformatting on the medical image volume. In particular, the computerized tool can electronically execute a deep learning neural network on the medical image volume, where the deep learning neural network can be configured and/or trained to generate three distinct outputs based on the medical image volume: localizations/segmentations of a set of anatomical landmarks depicted in the medical image volume as a first output, localizations/segmentations of a set of principal anatomical planes depicted in the medical image volume as a second output, and localizations/segmentations of a set of organs depicted in the medical image volume as a third output. In various aspects, the computerized tool can determine a current anatomical orientation of the medical image volume by leveraging such three distinct outputs. More specifically, the computerized tool can determine a first estimated anatomical orientation of the medical image volume based on the set of anatomical landmark localizations, the computerized tool can determine a second estimated anatomical orientation of the medical image volume based on the set of principal anatomical plane localizations, and the computerized tool can determine a third estimated anatomical orientation of the medical image volume based on the set of organ segmentations. Accordingly, in various instances, the computerized tool can aggregate (e.g., average) such three estimated anatomical orientations together, and the result of such aggregation can be considered as the current anatomical orientation of the medical image volume. In various cases, the computerized tool can then rotate and/or translate the medical image volume, such that the current anatomical orientation matches, after such rotation and/or translation, any suitable orientation as desired.

In various aspects, because the computerized tool can utilize deep learning to generate three distinct outputs (e.g., anatomical landmark localizations, principal anatomical plane localizations, and organ segmentations), and because the computerized tool can compute three distinct estimations of the current anatomical orientation of the medical image volume based on such three distinct outputs, the computerized tool can be considered as implementing a multi-pronged (e.g., three-pronged) multi-planar reformatting technique. Such multi-pronged multi-planar reformatting technique can be considered as including a level of redundancy and/or reformatting diversification that can result in improved accuracy of medical image volume reorientation.

For example, suppose that a deep learning technique were to perform multi-planar reformatting based only upon organ segmentations (e.g., such deep learning technique might segment a set of organs depicted within a medical image volume and then rotate/translate the medical image volume until the segmented organs achieve a desired orientation). Such a deep learning technique would be considered as non-redundant and/or as otherwise lacking in reformatting diversification, precisely because such a deep learning technique would rely entirely and/or solely upon organ segmentation. In other words, if the organs depicted in a medical image volume are incorrectly, inaccurately, and/or otherwise imprecisely segmented, then the subsequent rotations of the medical image volume (which rotations would be based only on such organ segmentations) can cause the medical image volume to exhibit an undesired orientation rather than a desired orientation. In still other words, and as the present inventors recognized, such a deep learning technique would be considered as putting all its multi-planar reformatting "eggs" into the organ segmentation "basket" (e.g., such a technique would yield improper reformatting/reorientation results whenever an organ segmentation inaccuracy occurs).

As another example, suppose that a deep learning technique were to instead perform multi-planar reformatting based only upon anatomical landmark localization (e.g., such deep learning technique might localize a set of anatomical landmarks depicted within a medical image volume and then rotate/translate the medical image volume until the localized anatomical landmarks achieve a desired orientation). As above, such a deep learning technique would also be considered as non-redundant and/or as otherwise lacking in reformatting diversification, precisely because such a deep learning technique would rely entirely and/or solely upon landmark localization. In other words, if the anatomical landmarks depicted in a medical image volume are incorrectly, inaccurately, and/or otherwise imprecisely localized, then the subsequent rotations of the medical image volume (which rotations would be based only on such anatomical landmarks) can cause the medical image volume to exhibit an undesired orientation rather than a desired orientation. In still other words, and as the present inventors recognized, such a deep learning technique would be considered as putting all its multi-planar reformatting "eggs" into the landmark localization "basket" (e.g., such a technique would yield improper reformatting/reorientation results whenever a landmark localization inaccuracy occurs).

As yet another example, suppose that a deep learning technique were to instead perform multi-planar reformatting based only upon principal anatomical plane localization (e.g., such deep learning technique might localize a set of principal anatomical planes depicted within a medical image volume and then rotate/translate the medical image volume until the localized principal anatomical planes achieve a desired orientation). Just like above, such a deep learning technique would be considered as non-redundant and/or as otherwise lacking in reformatting diversification, precisely because such a deep learning technique would rely entirely and/or solely upon principal plane localization. In other words, if the principal anatomical planes depicted in a medical image volume are incorrectly, inaccurately, and/or otherwise imprecisely localized, then the subsequent rotations of the medical image volume (which rotations would be based only on such principal anatomical planes) can cause the medical image volume to exhibit an undesired orientation rather than a desired orientation. In still other words, and as the present inventors recognized, such a deep learning technique would be considered as putting all its multi-planar reformatting "eggs" into the principal plane localization "basket" (e.g., such a technique would yield improper reformatting/reorientation results whenever a plane localization inaccuracy occurs).

In stark contrast, the computerized tool described herein can utilize a deep learning multi-planar reformatting technique, which exhibits increased redundancy and/or increased reformatting diversification, and which redundancy and/or reformatting diversification can help to improve reorientation accuracy. In other words, because the computerized tool described herein can rely upon all three of anatomical landmark localization, principal anatomical plane localization, and organ segmentation, the computerized tool can be better able to preserve and/or safeguard reorientation accuracy against localization and/or segmentation inaccuracies. For instance, suppose that the computerized tool were to inaccurately segment the set of organs. In such case, the computerized tool can nevertheless determine the current anatomical orientation of the medical image volume with sufficient accuracy (e.g., provided that the set of anatomical landmarks and the set of principal anatomical planes are accurately localized). Thus, the computerized tool can be considered as being robust against organ segmentation inaccuracies (e.g., can be considered as not placing all its multi-planar reformatting "eggs" into the organ segmentation "basket"). As another example, suppose that the computerized tool were to instead inaccurately localize the set of principal anatomical planes. In such case, the computerized tool can nevertheless determine the current anatomical orientation of the medical image volume with sufficient accuracy (e.g., provided that the set of anatomical landmarks and the set of organs are accurately localized/segmented). Thus, the computerized tool can be considered as being robust against plane localization inaccuracies (e.g., can be considered as not placing all its multi-planar reformatting "eggs" into the plane localization "basket"). As still another example, suppose that the computerized tool were to inaccurately localize the set of anatomical landmarks. In such case, the computerized tool can nevertheless determine the current anatomical orientation of the medical image volume with sufficient accuracy (e.g., provided that the set of principal anatomical planes and the set of organs are accurately localized/segmented). Thus, the computerized tool can be considered as being robust against landmark localization inaccuracies (e.g., can be considered as not placing all its multi-planar reformatting "eggs" into the landmark localization "basket"). In short, because the computerized tool can rely upon all three of landmark localization, plane localization, and organ segmentation, and because the likelihood of inaccurately performing two or more of such three tasks can be significantly lower than the likelihood of inaccurately performing only one of such three tasks, the computerized tool can be considered as demonstrating a level of redundancy and/or diversification that can help to safeguard and/or preserve reformatting/reorientation accuracy.

In various embodiments, the computerized tool described herein can comprise a receiver component, a detection component, an orientation component, and/or an execution component.

In various embodiments, there can be a three-dimensional medical image. In various aspects, the three-dimensional medical image can be a three-dimensional array of voxels (e.g., a stack of two-dimensional pixel arrays) that depicts any suitable anatomical structure (e.g., head, chest, arm, leg, torso, abdomen) and/or any suitable portion thereof of a medical patient (e.g., human, animal, and/or otherwise) as desired. In various instances, the three-dimensional medical image can have any suitable number of voxels arranged in any suitable layout as desired. In various cases, the three-dimensional medical image can have been generated and/or captured by any suitable imaging modality and/or imaging equipment as desired (e.g., can have been generated/captured by a CT scanner, an X-ray scanner, an MRI scanner, a PET scanner, and/or an ultrasound scanner).

In any case, it can be desired to perform multi-planar reformatting on the three-dimensional medical image. In other words, it can be desired to reorient the three-dimensional medical image such that the depicted anatomical structure is rotated to match a predetermined and/or desired orientation. As described herein, the computerized tool can facilitate such multi-planar reformatting and/or reorientation.

In various embodiments, the receiver component of the computerized tool can electronically receive and/or otherwise electronically access the three-dimensional medical image. In some instances, the receiver component can electronically retrieve the three-dimensional medical image from any suitable centralized and/or decentralized data structure (e.g., graph data structure, relational data structure, hybrid data structure), whether remote from and/or local to the receiver component. In other instances, the receiver component can electronically retrieve the three-dimensional medical image from any suitable imaging device (e.g., X-ray scanner, CT scanner, MRI scanner, ultrasound scanner, PET scanner) that captured/generated the three-dimensional medical image. In any case, the receiver component can electronically obtain and/or access the three-dimensional medical image, such that other components of the computerized tool can electronically interact with (e.g., read, write, edit, manipulate) the three-dimensional medical image.

In various embodiments, the detection component of the computerized tool can electronically store, electronically maintain, electronically control, and/or otherwise electronically access a machine learning model. In various aspects, the machine learning model can exhibit any suitable artificial intelligence architecture as desired. For example, the machine learning model can exhibit a deep learning neural network architecture. In such case, the machine learning model can include any suitable number of layers (e.g., input layer, one or more hidden layers, output layer), can include any suitable numbers of neurons in various layers (e.g., different layers can have the same and/or different numbers of neurons as each other), can include any suitable activation functions (e.g., softmax, sigmoid, hyperbolic tangent, rectified linear unit) in various neurons (e.g., different neurons can have the same and/or different activation functions as each other), and/or can include any suitable interneuron connections (e.g., forward connections, skip connections, recurrent connections).

In any case, the machine learning model can be configured to receive as input the three-dimensional medical image, and to produce three distinct outputs based on the three-dimensional medical image. A first output of the machine learning model can be a set of anatomical landmark localizations; that is, the first output can be localizations/segmentations of a set of anatomical landmarks that are depicted in the three-dimensional medical image. The set of anatomical landmarks can include any suitable number of anatomical landmarks. Moreover, an anatomical landmark can be any suitable biologically-meaningful locus that is visually illustrated, depicted, and/or otherwise shown within the three-dimensional medical image (e.g., a nasion landmark, an external auditory canal landmark, a cochlea landmark). Accordingly, the machine learning model can be considered as being able to detect and/or localize within the three-dimensional medical image each of the set of anatomical landmarks (e.g., can be considered as being able to determine where each of the set of anatomical landmarks is physically positioned and/or physically located within the three-dimensional medical image).

A second output of the machine learning model can be a set of principal anatomical plane localizations; that is, the second output can be localizations/segmentations of a set of principal anatomical planes that are depicted in the three-dimensional medical image. The set of principal anatomical planes can include any suitable number of principal anatomical planes. Furthermore, a principal anatomical plane can be any suitable cross-sectional plane that transects, in any suitable and/or desired fashion, the anatomical structure that is depicted in the three-dimensional medical image (e.g., a sagittal plane, a coronal plane, a transverse plane, an oblique plane). Accordingly, the machine learning model can be considered as being able to detect and/or localize within the three-dimensional medical image each of the set of principal anatomical planes (e.g., can be considered as being able to determine where each of the set of principal anatomical planes is physically positioned and/or physical located within the three-dimensional medical image).

A third output of the machine learning model can be a set of organ segmentations; that is, the third output can be localizations/segmentations of a set of organs that are depicted in the three-dimensional medical image. The set of organs can include any suitable number of organs. In various cases, organ segmentations can be any suitable voxel-wise masks that indicate to which biological organs various individual voxels of the three-dimensional medical image belong (e.g., a brain segmentation, an eye segmentation, an ear segmentation, a skull segmentation, a nose segmentation, a tongue segmentation, a lung segmentation, a spine segmentation). Accordingly, the machine learning model can be considered as being able to detect and/or localize within the three-dimensional medical image each of the set of organs (e.g., can be considered as being able to determine where each of the set of organs is physically positioned and/or physically located within the three-dimensional medical image).

In any case, the detection component can electronically generate the set of anatomical landmark localizations, the set of principal anatomical plane localizations, and the set of organ segmentations by executing the machine learning model on the three-dimensional medical image. More specifically, in various aspects, the detection component can feed the three-dimensional medical image to an input layer of the machine learning model, the three-dimensional medical image can complete a forward pass through one or more hidden layers of the machine learning model, and an output layer of the machine learning model can compute the set of anatomical landmark localizations, the set of principal anatomical plane localizations, and the set of organ segmentations based on activations from the one or more hidden layers.

In various embodiments, the orientation component of the computerized tool can electronically determine a current anatomical orientation of the three-dimensional medical image, based on the set of anatomical landmark localizations, the set of principal anatomical plane localizations, and the set of organ segmentations.

More specifically, in the various aspects, the orientation component can determine a first estimated anatomical orientation based on the set of anatomical landmark localizations. In various instances, such determination can be facilitated analytically. That is, the geometric arrangement/layout of the set of anatomical landmarks (e.g., the geometric interrelationships between various pairs of the set of anatomical landmarks) can convey and/or otherwise indicate how the anatomical structure is currently oriented in the three-dimensional medical image. In light of this disclosure, those having ordinary skill in the art will appreciate how to compute and/or estimate an orientation of a particular anatomical structure when given a set of anatomical landmark localizations associated with the particular anatomical structure. Moreover, those having ordinary skill in the art will further appreciate that the first estimated anatomical orientation can be expressed in any suitable format and/or dimensionality as desired (e.g., can be one or more scalars, vectors, matrices, and/or tensors).

Furthermore, in the various cases, the orientation component can determine a second estimated anatomical orientation based on the set of principal anatomical plane localizations. In various aspects, such determination can be facilitated analytically. That is, the geometric arrangement/layout of the set of principal anatomical planes can convey and/or otherwise indicate how the anatomical structure is currently oriented in the three-dimensional medical image. As above, those having ordinary skill in the art will appreciate, in light of this disclosure, how to compute and/or estimate an orientation of a particular anatomical structure when given a set of principal anatomical plane localizations associated with the particular anatomical structure. Moreover, those having ordinary skill in the art will further appreciate that the second estimated anatomical orientation can be expressed in any suitable format and/or dimensionality as desired (e.g., can be one or more scalars, vectors, matrices, and/or tensors).

Further still, in various instances, the orientation component can determine a third estimated anatomical orientation based on the set of organ segmentations. In various cases, such determination can be facilitated analytically. That is, the geometric arrangement/layout of the set of organs can convey and/or otherwise indicate how the anatomical structure is currently oriented in the three-dimensional medical image. Again, those having ordinary skill in the art will appreciate, in light of this disclosure, how to compute and/or estimate an orientation of a particular anatomical structure when given a set of organ segmentations associated with the particular anatomical structure. Moreover, those having ordinary skill in the art will further appreciate that the third estimated anatomical orientation can be expressed in any suitable format and/or dimensionality as desired (e.g., can be one or more scalars, vectors, matrices, and/or tensors).

In various aspects, the orientation component can aggregate together the first estimated anatomical orientation, the second estimated anatomical orientation, and the third estimated anatomical orientation, and such aggregation can be considered as the current anatomical orientation of the anatomical structure. For example, in some cases, the orientation component can compute an average of the first estimated anatomical orientation, the second estimated anatomical orientation, and the third estimated anatomical orientation, and the current anatomical orientation can be equal to and/or otherwise based on such average.

Because the current anatomical orientation can be based on all three of the first estimated anatomical orientation, the second estimated anatomical orientation, and the third estimated anatomical orientation, the current anatomical orientation can be considered as being robust and/or safeguarded against inaccuracies in any one of the first estimated anatomical orientation, the second estimated anatomical orientation, and the third estimated anatomical orientation. For example, even if the first estimated anatomical orientation is inaccurate (e.g., which can occur when the machine learning model of the detection component improperly/inaccurately localizes the set of anatomical landmarks), the current anatomical orientation can nevertheless be sufficiently accurate (e.g., if the second estimated anatomical orientation and the third estimated anatomical orientation are both accurate, then they can be considered as compensating for an inaccuracy in the first estimated anatomical orientation). As another example, even if the second estimated anatomical orientation is inaccurate (e.g., which can occur when the machine learning model of the detection component improperly/inaccurately localizes the set of principal anatomical planes), the current anatomical orientation can nevertheless be sufficiently accurate (e.g., if the first estimated anatomical orientation and the third estimated anatomical orientation are both accurate, then they can be considered as compensating for an inaccuracy in the second estimated anatomical orientation). As yet another example, even if the third estimated anatomical orientation is inaccurate (e.g., which can occur when the machine learning model of the detection component improperly/inaccurately segments the set of organs), the current anatomical orientation can nevertheless be sufficiently accurate (e.g., if the first estimated anatomical orientation and the second estimated anatomical orientation are both accurate, then they can compensate for an inaccuracy in the third estimated anatomical orientation).

In various embodiments, the execution component of the computerized tool can electronically rotate and/or translate the three-dimensional medical image, based on the current anatomical orientation. For example, in various instances, it can be desired to display and/or present the anatomical structure of the three-dimensional medical image (and/or a cross-sectional plane thereof) according to a particular orientation. In some aspects, the particular orientation can be any suitable orientation as desired (e.g., can be a predetermined and/or fixed orientation, can be a user-defined orientation). In any case, because the orientation component can have computed the current anatomical orientation of the three-dimensional medical image, the execution component can determine and/or otherwise know how to manipulate (e.g., can determine and/or know about which axes and/or by what angles to rotate) the three-dimensional medical image, such that the anatomical structure exhibits the particular orientation post-manipulation. In various instances, once the anatomical structure of the three-dimensional medical image has been rotated/translated so as to match the particular orientation, the execution component can electronically render the three-dimensional medical image (and/or any suitable cross-sectional planes thereof) on any suitable computer screens/displays/monitors as desired. In other instances, once the anatomical structure of the three-dimensional medical image has been rotated/translated so as to match the particular orientation, the execution component can electronically transmit the three-dimensional medical image (and/or any suitable cross-sectional planes thereof) to any suitable computing devices as desired.

In various embodiments, the computerized tool can further comprise a training component that can train (e.g., in supervised fashion) the machine learning model of the detection component, so that the machine learning model can learn how to accurately localize/segments anatomical landmarks, principal anatomical planes, and organs that are depicted in three-dimensional medical images. Such training is described in more detail herein.

Accordingly, various embodiments described herein can be considered as a computerized tool that can electronically receive a medical image volume; that can electronically localize/segment, via deep learning, anatomical landmarks illustrated within the medical image volume; that can electronically localize/segment, via deep learning, principal anatomical planes illustrated within the medical image volume; that can electronically localize/segment, via deep learning, organs illustrated within the medical image volume; and that electronically perform reformatting and/or reorientation of the medical image volume based on the localizations/segmentations of the anatomical landmarks, the principal anatomical planes, and/or the organs. Such a computerized tool can be considered as facilitating a multi-pronged reformatting and/or reorientation technique whose redundancy and/or reformatting diversification can help to improve and/or safeguard reformatting/reorientation accuracy.

Various embodiments of the subject innovation can be employed to use hardware and/or software to solve problems that are highly technical in nature (e.g., to facilitate deep learning multi-planar reformatting of medical images), that are not abstract and that cannot be performed as a set of mental acts by a human. Further, some of the processes performed can be performed by a specialized computer (e.g., deep learning neural network) for carrying out defined tasks related to deep learning multi-planar reformatting of medical images. For example, such defined tasks can include: accessing, by a device operatively coupled to a processor, a three-dimensional medical image; localizing, by the device and via execution of a machine learning model, a set of landmarks depicted in the three-dimensional medical image, a set of principal anatomical planes depicted in the three-dimensional medical image, and a set of organs depicted in the three-dimensional medical image; and determining, by the device, an anatomical orientation exhibited by the three-dimensional medical image, based on the set of landmarks, the set of principal anatomical planes, and/or the set of organs. In various cases, such defined tasks can further include: rotating, by the device, the three-dimensional medical image, such that the anatomical orientation now matches a predetermined anatomical orientation.

Such defined tasks are not performed manually by humans. Indeed, neither the human mind nor a human with pen and paper can electronically receive a medical image volume (e.g., an X-ray voxel array, a CT voxel array, an MRI voxel array, a PET voxel array), electronically execute a machine learning model (e.g., a neural network) on the medical image volume thereby yielding a set of anatomical landmark localizations, a set of principal anatomical plane localizations, and a set of organ segmentations, and electronically reformat and/or reorient the medical image volume based on the set of anatomical landmark localizations, the set of principal anatomical plane localizations, and/or the set of organ segmentations. Instead, various embodiments of the subject innovation are inherently and inextricably tied to computer technology and cannot be implemented outside of a computing environment (e.g., a deep learning neural network is an inherently computerized construct that cannot be trained and/or executed in any way without computers; a computerized tool that utilizes a deep learning neural network to facilitate multi-planar reformatting of medical image volumes is likewise inherently computerized and cannot be implemented in any sensible, practical, or reasonable way without computers).

Moreover, various embodiments of the subject innovation can integrate into a practical application various teachings described herein relating to deep learning multi-planar reformatting of medical images. As explained above, the computerized tool described herein can be considered as facilitating a deep learning multi-planar reformatting technique that can help to safeguard reformatting/reorientation accuracy. In particular, the computerized tool can determine a current anatomical orientation of a medical image volume based on a set of anatomical landmark localizations of the medical image volume, based on a set of principal anatomical plane localizations of the medical image volume, and based on a set of organ segmentations of the medical image volume. Specifically, the computerized tool can compute a first estimated orientation based on the set of anatomical landmark localizations, can compute a second estimated orientation based on the set of principal anatomical plane localizations, and can compute a third estimated orientation based on the set of organ segmentations. Moreover, the computerized tool can aggregate the first, second, and third estimated orientations together to form the current anatomical orientation. Thus, if any one of the first, second, and third estimated orientations is incorrect/inaccurate, it is nevertheless possible for the other two estimated orientations to compensate for such incorrectness/inaccuracy. For example, even if the computerized tool erroneously localizes anatomical landmarks in the medical image volume, the computerized tool can nevertheless identify the current anatomical orientation with sufficient accuracy, provided that the computerized tool correctly localizes/segments the principal anatomical planes and/or the organs in the medical image volume. That is, the computerized tool can be considered as robust against landmark localization inaccuracies. As another example, even if the computerized tool erroneously localizes principal anatomical planes in the medical image volume, the computerized tool can nevertheless identify the current anatomical orientation with sufficient accuracy, provided that the computerized tool correctly localizes/segments the anatomical landmarks and/or the organs in the medical image volume. That is, the computerized tool can be considered as robust against principal plane localization inaccuracies. As yet another example, even if the computerized tool erroneously segments organs in the medical image volume, the computerized tool can nevertheless identify the current anatomical orientation with sufficient accuracy, provided that the computerized tool correctly localizes the anatomical landmarks and/or the principal anatomical planes in the medical image volume. That is, the computerized tool can be considered as robust against organ segmentation inaccuracies. Therefore, the computerized tool can be considered as being better able to safeguard and/or protect the accuracy of medical image reformatting/reorientation, as compared to techniques that do not implement the herein-described deep learning technique. Such a computerized tool constitutes a concrete and tangible technique improvement in the field of multi-planar reformatting and thus certainly qualifies as a useful and practical application of computers.

Furthermore, various embodiments of the subject innovation can control real-world tangible devices based on the disclosed teachings. For example, various embodiments of the subject innovation can electronically receive real-world medical image volumes (e.g., real-world X-ray voxel arrays, real-world CT voxel arrays, real-world MRI voxel arrays), can electronically execute a real-world neural network on such real-world medical image volumes to yield landmark localizations, principal plane localizations, and organ segmentations, and can electronically reorient (e.g., rotate) such real-world medical image volumes based on such landmark localizations, principal plane localizations, and organ segmentations. In some cases, various embodiments of the subject innovation can electronically render the reoriented (e.g., rotated) versions of such real-world medical image volumes on real-world computer screens/displays/monitors.

It should be appreciated that the herein figures and description provide non-limiting examples of the subject innovation and are not necessarily drawn to scale.

FIG. 1 illustrates a block diagram of an example, non-limiting system 100 that can facilitate deep learning multi-planar reformatting for medical images in accordance with one or more embodiments described herein. As shown, a multi-planar reformatting system 102 can be electronically integrated, via any suitable wired and/or wireless electronic connections, with a 3D medical image 104 and/or with a desired anatomical orientation 106.

In various embodiments, the 3D medical image 104 can be any suitable three-dimensional array of voxels that depicts, illustrates, and/or otherwise visually represents any suitable anatomical structure and/or portion thereof of a medical patient. Non-limiting examples of an anatomical structure can include a head of the medical patient, a neck of the medical patient, a limb of the medical patient, an appendage of the medical patient, a torso of the medical patient, a chest of the medical patient, an abdomen of the medical patient, a shoulder of the medical patient, an elbow of the medical patient, a wrist of the medical patient, a knee of the medical patient, and/or an ankle of the medical patient. In various aspects, the 3D medical image 104 can have any suitable number of voxels arranged in any suitable layout as desired. That is, the 3D medical image 104 can be an a-by-b-by-c voxel array, for any suitable positive integers a, b, and c. In various instances, the 3D medical image 104 can be generated and/or captured by any suitable medical imaging modality (not shown) as desired. Non-limiting examples of medical imaging modalities that can generate/capture the 3D medical image 104 can include an X-ray scanner, a CT scanner, an MRI scanner, a PET scanner, and/or an ultrasound scanner.

In various embodiments, the desired anatomical orientation 106 can be any suitable orientation that is desired to be exhibited by the anatomical structure depicted in the 3D medical image 104. In other words, the 3D medical image 104 can depict and/or illustrate the anatomical structure of the medical patient according to some current anatomical orientation, and it can be desired to rotate, reorient, and/or otherwise reformat the 3D medical image 104 such that the anatomical structure is instead depicted according to the desired anatomical orientation 106. In various instances, the desired anatomical orientation 106 can be expressed in any suitable data format as desired. For example, in some cases, the desired anatomical orientation 106 can be expressed as one or more scalars, one or more vectors, one or more matrices, one or more tensors, one or more character strings, and/or any suitable combination thereof. In various aspects, the desired anatomical orientation 106 can be fixed and/or predetermined in any suitable fashion. In various instances, the desired anatomical orientation 106 can be user-defined (e.g., can be indicated by user-provided input).

Figure 2:
FIG. 2 illustrates an example, non-limiting block diagram showing a two-dimensional slice of a medical image according to two different orientations in accordance with one or more embodiments described herein.
Figure 2:
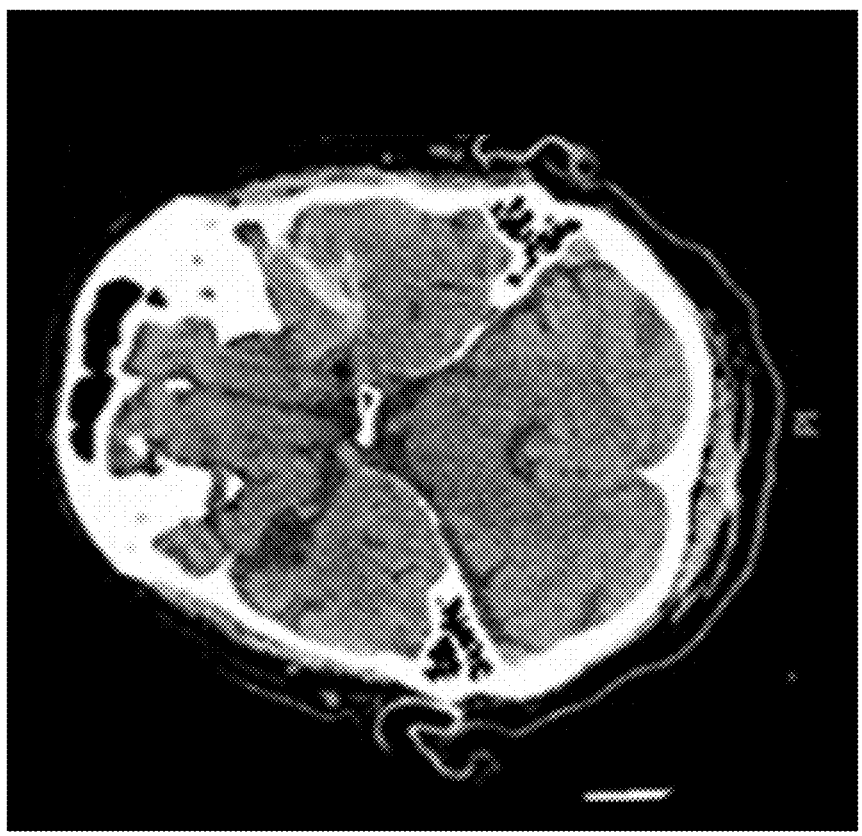

FIG. 2 illustrates an example, non-limiting block diagram 200 showing a two-dimensional slice of a medical image according to two different orientations in accordance with one or more embodiments described herein. In other words, FIG. 2 helps to show why rotating, reorienting, and/or reformatting a medical image can be desirable.

FIG. 2 depicts a CT slice 202 and a CT slice 204. As shown, both the CT slice 202 and the CT slice 204 illustrate transverse cross-sectional planes of a CT scan of a medical patient's skull. As can be seen, the difference between the CT slice 202 and the CT slice 204 is that the CT slice 202 illustrates the medical patient's skull according to some skewed orientation (e.g., the skull is oriented with a slight clockwise tilt in the CT slice 202), while the CT slice 204 instead illustrates the medical patient's skull according to some desired orientation (e.g., the skull is oriented with no clockwise or counterclockwise tilt in the CT slice 204). Thus, in various cases, the CT slice 202 can be considered as a two-dimensional cross-section of a three-dimensional medical image that depicts the medical patient's skull according to some current, non-aligned orientation, and the CT slice 204 can instead be considered as a two-dimensional cross-section of that same three-dimensional medical image after having been rotated to a desired, aligned orientation. In other words, the CT slice 202 can be considered as showing a two-dimensional slice of a non-limiting example of the 3D medical image 104, and the CT slice 204 can be considered as showing how that same two-dimensional slice would appear if rotated to be in accordance with a non-limiting example of the desired anatomical orientation 106.

Referring back to FIG. 1, in any case, it can be desired to rotate, reorient, and/or otherwise reformat the 3D medical image 104 so as to be in accordance with the desired anatomical orientation 106. As described herein, the multi-planar reformatting system 102 can facilitate such rotation, reorientation, and/or reformatting.

In various embodiments, the multi-planar reformatting system 102 can comprise a processor 108 (e.g., computer processing unit, microprocessor) and a computer-readable memory 110 that is operably and/or operatively and/or communicatively connected/coupled to the processor 108. The computer-readable memory 110 can store computer-executable instructions which, upon execution by the processor 108, can cause the processor 108 and/or other components of the multi-planar reformatting system 102 (e.g., receiver component 112, detection component 114, orientation component 116, execution component 118) to perform one or more acts. In various embodiments, the computer-readable memory 110 can store computer-executable components (e.g., receiver component 112, detection component 114, orientation component 116, execution component 118), and the processor 108 can execute the computer-executable components.

In various embodiments, the multi-planar reformatting system 102 can comprise a receiver component 112. In various aspects, the receiver component 112 can electronically receive and/or otherwise electronically access the 3D medical image 104 and/or the desired anatomical orientation 106. In various instances, the receiver component 112 can electronically retrieve the 3D medical image 104 and/or the desired anatomical orientation 106 from any suitable centralized and/or decentralized data structure (not shown). In some aspects, the receiver component 112 can electronically retrieve the 3D medical image 104 from any suitable imaging devices (e.g., X-ray scanners, CT scanners, MRI scanners, ultrasound scanners, PET scanners) that captured and/or otherwise generated the 3D medical image 104. In some aspects, the receiver component 112 can electronically retrieve the desired anatomical orientation 106 from any suitable interface device (e.g., keyboard, keypad, touchscreen). In any case, the receiver component 112 can electronically obtain and/or access the 3D medical image 104 and/or the desired anatomical orientation 106, such that other components of the multi-planar reformatting system 102 can electronically interact with the 3D medical image 104 and/or the desired anatomical orientation 106.

In various embodiments, the multi-planar reformatting system 102 can comprise a detection component 114. In various aspects, as described herein, the detection component 114 can electronically execute a machine learning model on the 3D medical image 104, so as to generate a set of anatomical landmark localizations associated with the anatomical structure depicted in the 3D medical image 104, a set of principal anatomical plane localizations associated with the anatomical structure depicted in the 3D medical image 104, and a set of organ segmentations associated with the anatomical structure depicted in the 3D medical image 104.

In various embodiments, the multi-planar reformatting system 102 can further comprise an orientation component 116. In various instances, as described herein, the orientation component 116 can electronically determine a current anatomical orientation of the anatomical structure based on the set of anatomical landmark localizations, the set of principal anatomical plane localizations, and/or the set of organ segmentations.

In various embodiments, the multi-planar reformatting system 102 can further comprise an execution component 118. In various cases, as described herein, the execution component 118 can electronically rotate and/or reorient the 3D medical image 104 based on the current anatomical orientation, such that the anatomical structure depicted in the 3D medical image 104 is now in accordance with the desired anatomical orientation 106.

Figure 3:
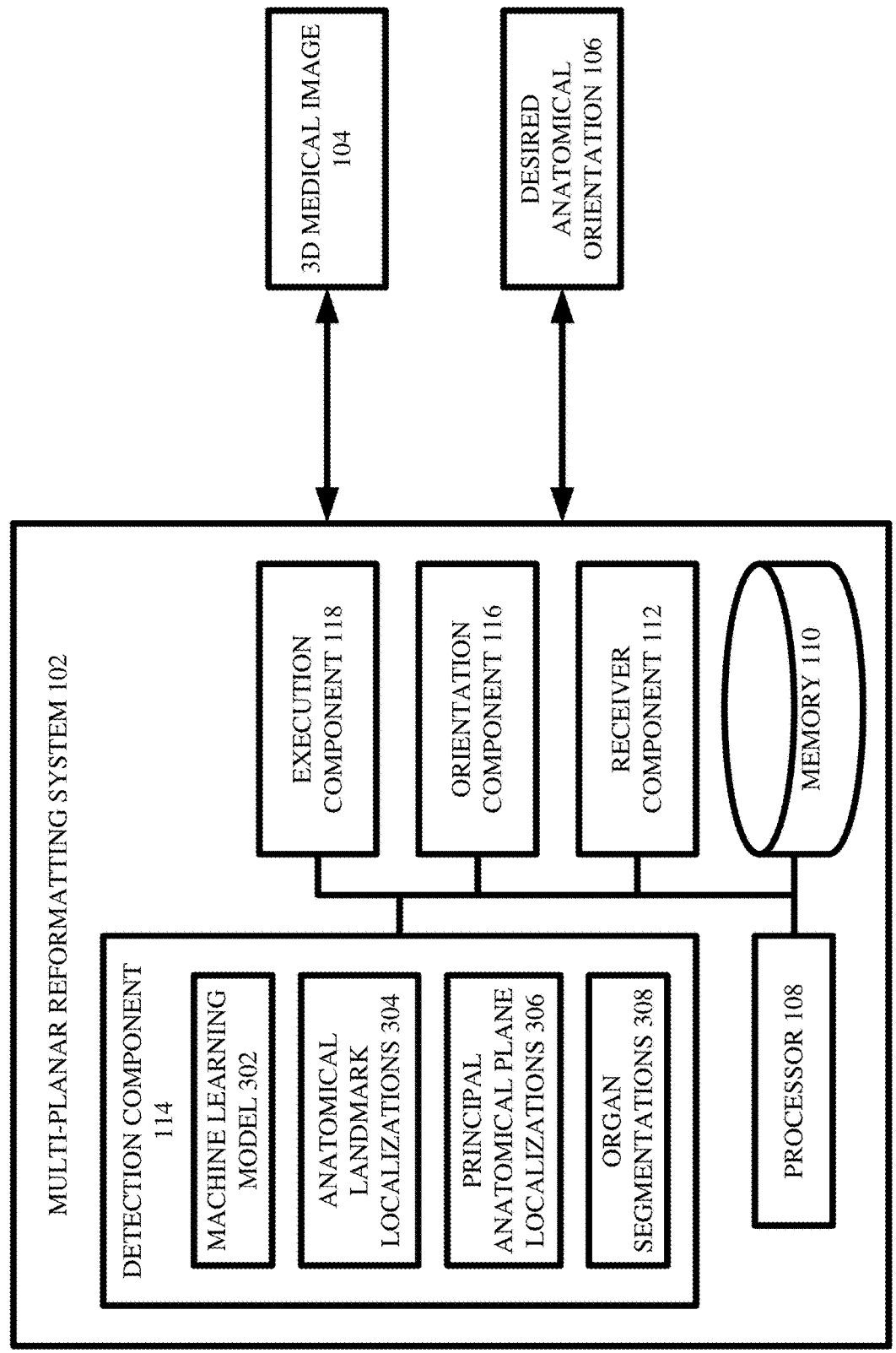
FIG. 3 illustrates a block diagram of an example, non-limiting system including a machine learning model, a set of anatomical landmark localizations, a set of principal anatomical plane localizations, and/or a set of organ segmentations that facilitates deep learning multi-planar reformatting for medical images in accordance with one or more embodiments described herein.

FIG. 3 illustrates a block diagram of an example, non-limiting system 300 including a machine learning model, a set of anatomical landmark localizations, a set of principal anatomical plane localizations, and/or a set of organ segmentations that can facilitate deep learning multi-planar reformatting for medical images in accordance with one or more embodiments described herein. As shown, the system 300 can, in some cases, comprise the same components as the system 100, and can further comprise a machine learning model 302, a set of anatomical landmark localizations 304, a set of principal anatomical plane localizations 306, and/or a set of organ segmentations 308.

In various embodiments, the detection component 114 can electronically store, electronically maintain, electronically control, and/or otherwise electronically access the machine learning model 302. In various instances, the detection component 114 can electronically execute the machine learning model 302 on the 3D medical image 104, thereby yielding the set of anatomical landmark localizations 304, the set of principal anatomical plane localizations 306, and/or the set of organ segmentations 308. This is further explained with respect to FIGS. 4-7.

Figure 4:
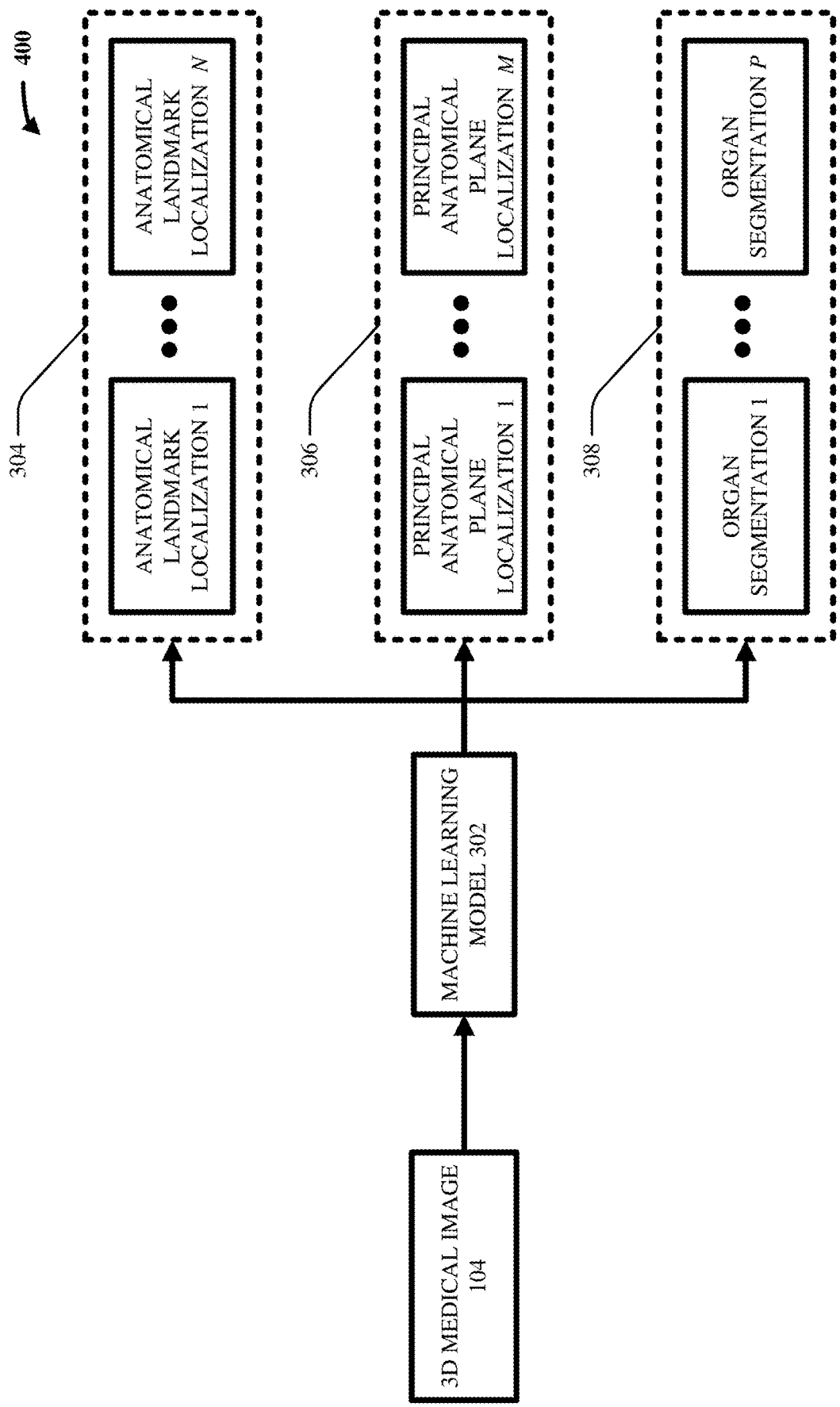
FIG. 4 illustrates an example, non-limiting block diagram showing how a machine learning model can generate a set of anatomical landmark localizations, a set of principal anatomical plane localizations, and/or a set of organ segmentations in accordance with one or more embodiments described herein.

FIG. 4 illustrates an example, non-limiting block diagram 400 showing how the machine learning model 302 can generate the set of anatomical landmark localizations 304, the set of principal anatomical plane localizations 306, and/or the set of organ segmentations 308 in accordance with one or more embodiments described herein.

In various aspects, the machine learning model 302 can have any suitable artificial intelligence architecture as desired. For example, the machine learning model 302 can be a deep learning neural network that has any suitable number of layers, any suitable numbers of neurons in various layers, any suitable activation functions in various neurons, and/or any suitable interneuron connectivity patterns. In various instances, the machine learning model 302 can be configured to receive as input the 3D medical image 104, and to produce as output all three of the set of anatomical landmark localizations 304, the set of principal anatomical plane localizations 306, and the set of organ segmentations 308. More specifically, in various aspects, an input layer of the machine learning model 302 can receive the 3D medical image 104, the 3D medical image 104 can complete a forward pass through one or more hidden layers of the machine learning model 302, and an output layer of the machine learning model 302 can compute the set of anatomical landmark localizations 304, the set of principal anatomical plane localizations 306, and the set of organ segmentations 308 based on activations provided by the one or more hidden layers.

As shown in FIG. 4, the set of anatomical landmark localizations 304 can include n landmark localizations for any suitable positive integer n: an anatomical landmark localization 1 to an anatomical landmark localization n. In various aspects, each anatomical landmark localization can convey, indicate, identify, and/or otherwise represent a position and/or location of a respectively corresponding anatomical landmark of the 3D medical image 104. For example, the anatomical landmark localization 1 can be one or more scalars, one or more vectors, one or more matrices, one or more tensors, and/or one or more character strings that indicate which voxels of the 3D medical image 104 belong to and/or otherwise make up a first anatomical landmark in the 3D medical image 104. In some cases, the anatomical landmark localization 1 can be a voxel-wise mask (e.g., like a segmentation mask) indicating which voxels of the 3D medical image 104 are part of the first anatomical landmark. Similarly, the anatomical landmark localization n can be one or more scalars, one or more vectors, one or more matrices, one or more tensors, and/or one or more character strings that represent which voxels of the 3D medical image 104 belong to and/or otherwise make up an n-th anatomical landmark in the 3D medical image 104. Again, in some cases, the anatomical landmark localization n can be a voxel-wise mask indicating which voxels of the 3D medical image 104 are part of the n-th anatomical landmark. As those having ordinary skill in the art will appreciate, an anatomical landmark can be any suitable biologically-meaningful locus that is visually illustrated, depicted, and/or otherwise shown within the 3D medical image 104. Non-limiting examples of anatomical landmarks can include a nasion landmark, an external auditory canal landmark, and/or a cochlea landmark.

Figure 5:
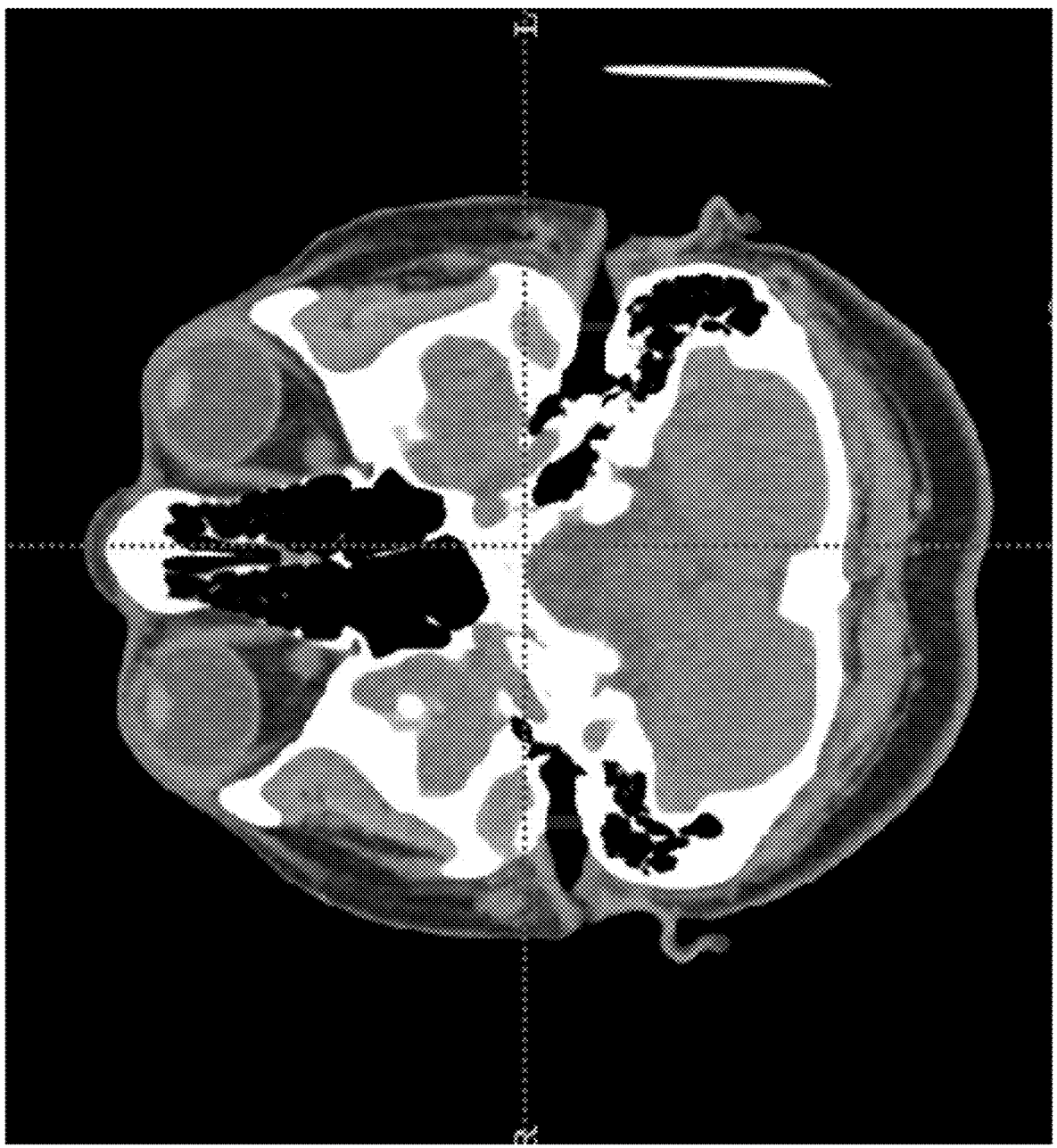
FIGS. 5-6 illustrate example, non-limiting diagrams of anatomical landmarks in accordance with one or more embodiments described herein.
Figure 6:
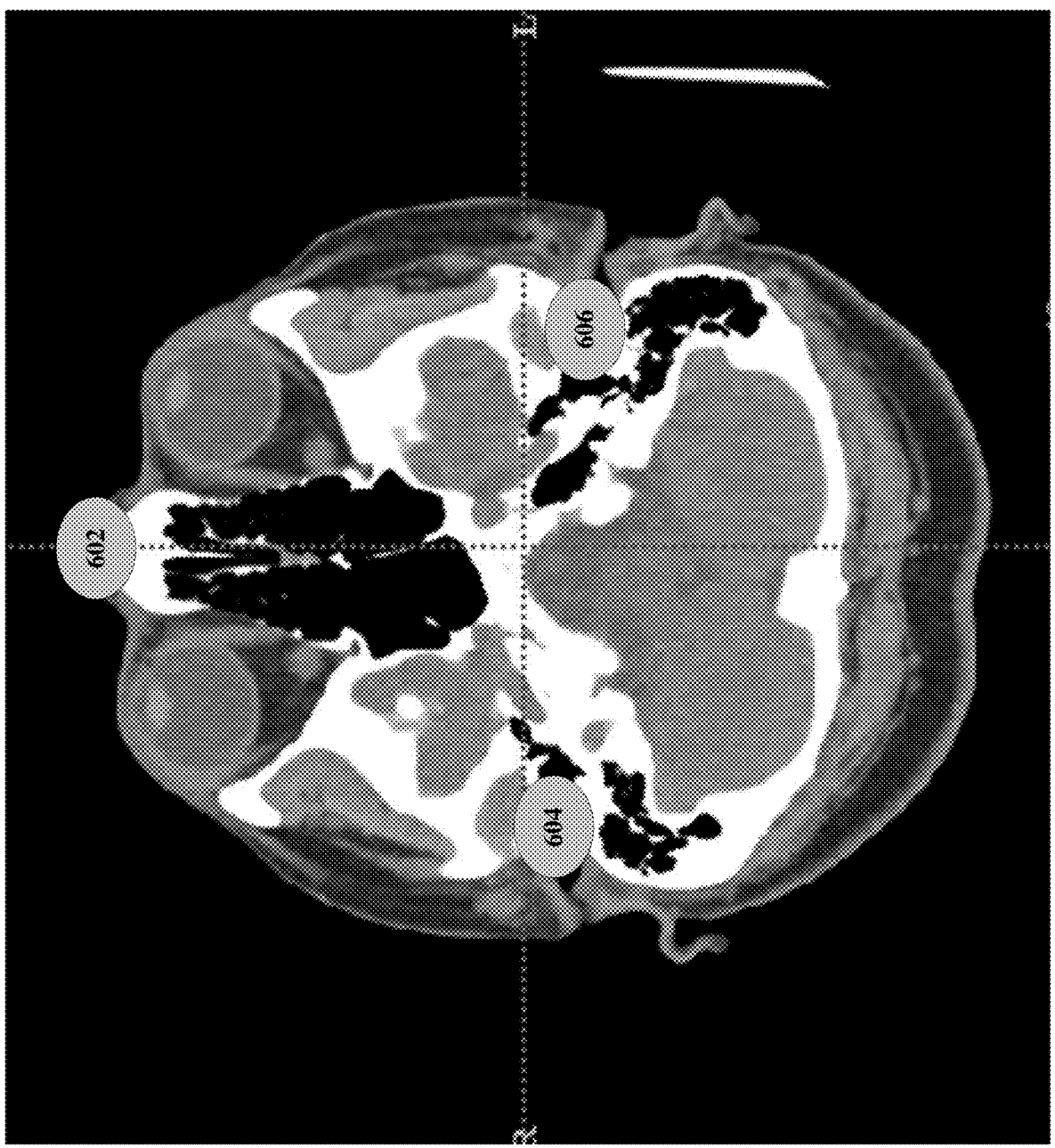

FIGS. 5-6 help to clarify the set of anatomical landmark localizations 304. As shown, FIG. 5 illustrates a CT slice 502 which depicts a medical patient's skull. As also shown, FIG. 6 illustrates the CT slice 502 with various anatomical landmarks called out for viewing convenience. Specifically, numeral 602 can be considered as calling out and/or otherwise indicating a nasion landmark of the CT slice 502, numeral 604 can be considered as calling out and/or otherwise indicating a right-side external auditory canal landmark of the CT slice 502, and numeral 606 can be considered as calling out and/or otherwise indicating a left-side external auditory canal landmark of the CT slice 502. As a non-limiting example that is for purposes of illustration, suppose that only such three landmarks were of concern. In such case, the set of anatomical landmark localizations 304 could have a cardinality of three. For instance, a first anatomical landmark localization of the set of anatomical landmark localizations 304 could correspond to a nasion landmark (e.g., could indicate/convey where the nasion landmark is located in the 3D medical image 104 and/or could otherwise indicate/convey which voxels of the 3D medical image 104 make up the nasion landmark). Moreover, a second anatomical landmark localization of the set of anatomical landmark localizations 304 could correspond to a right-side external auditory canal landmark (e.g., could indicate/convey where the right-side external auditory canal landmark is located in the 3D medical image 104 and/or could otherwise indicate/convey which voxels of the 3D medical image 104 make up the right-side external auditory canal landmark). Furthermore, a third anatomical landmark localization of the set of anatomical landmark localizations 304 could correspond to a left-side external auditory canal landmark (e.g., could indicate/convey where the left-side external auditory canal landmark is located in the 3D medical image 104 and/or could otherwise indicate/convey which voxels of the 3D medical image 104 make up the left-side external auditory canal landmark). Those having ordinary skill in the art will appreciate that FIGS. 5-6 are mere non-limiting examples for purposes of explanation.

Referring back to FIG. 4, the set of principal anatomical plane localizations 306 can include m plane localizations for any suitable positive integer m: a principal anatomical plane localization 1 to a principal anatomical plane localization m. In various aspects, each principal anatomical plane localization can convey, indicate, identify, and/or otherwise represent a position and/or location of a respectively corresponding principal anatomical plane of the 3D medical image 104. For example, the principal anatomical plane localization 1 can be one or more scalars, one or more vectors, one or more matrices, one or more tensors, and/or one or more character strings that indicate which voxels of the 3D medical image 104 belong to and/or otherwise make up a first principal anatomical plane in the 3D medical image 104. In some cases, the principal anatomical plane localization 1 can be a voxel-wise mask (e.g., like a segmentation mask) indicating which voxels of the 3D medical image 104 are part of the first principal anatomical plane. Similarly, the principal anatomical plane localization m can be one or more scalars, one or more vectors, one or more matrices, one or more tensors, and/or one or more character strings that indicate which voxels of the 3D medical image 104 belong to and/or otherwise make up an m-th principal anatomical plane in the 3D medical image 104. Again, n some cases, the principal anatomical plane localization m can be a voxel-wise mask indicating which voxels of the 3D medical image 104 are part of the m-th principal anatomical plane. As those having ordinary skill in the art will appreciate, a principal anatomical plane can be any suitable cross-sectional plane that transects, in any suitable and/or desired fashion, the anatomical structure that is depicted in the 3D medical image 104. Non-limiting examples of principal anatomical planes can include a sagittal plane, a coronal plane, a transverse plane, and/or an oblique plane.

Figure 7:
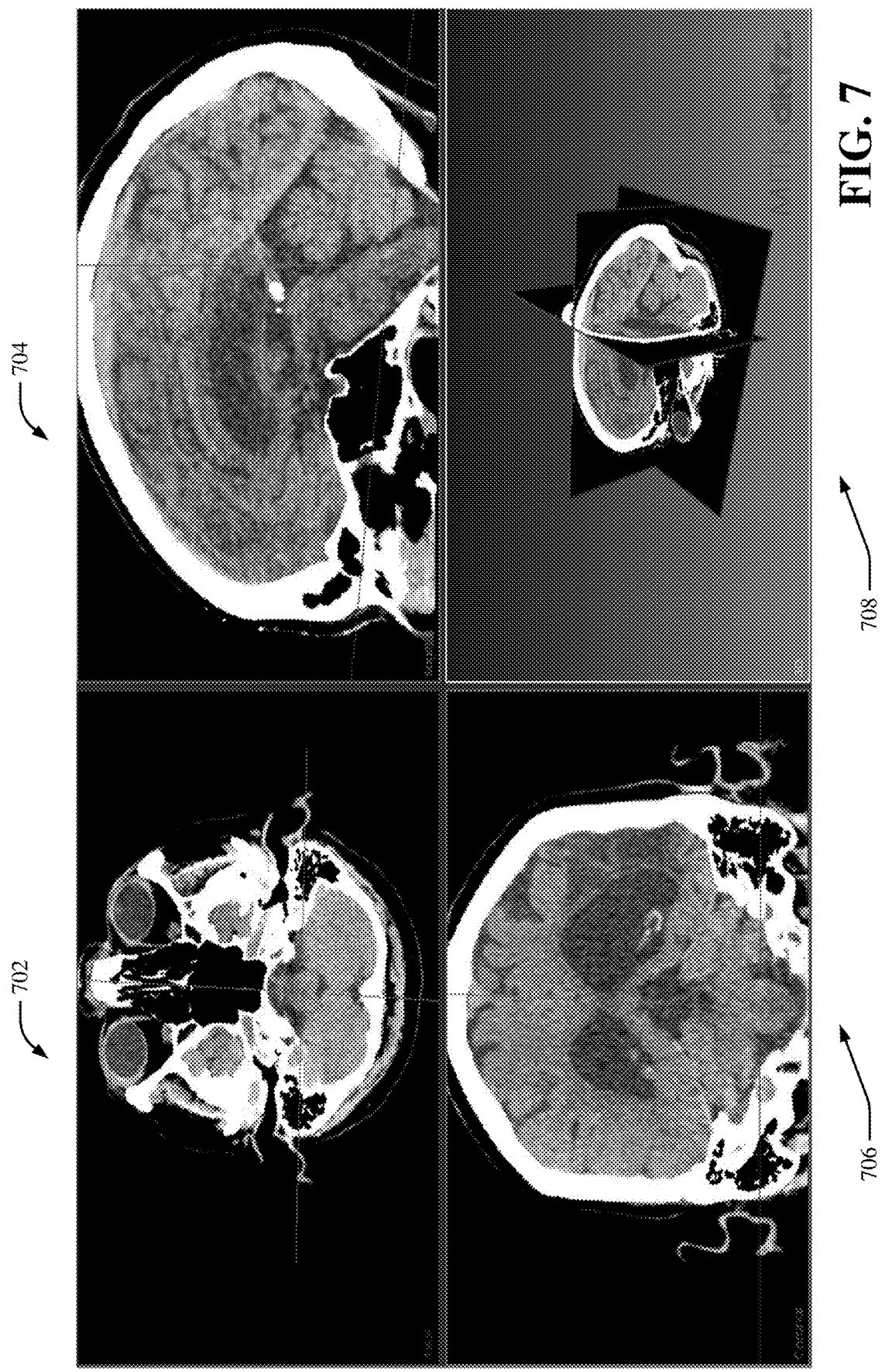
FIG. 7 illustrates an example, non-limiting diagram of principal anatomical planes in accordance with one or more embodiments described herein.

FIG. 7 helps to clarify the set of principal anatomical plane localizations 306. As shown, FIG. 7 illustrates a CT slice 702 that shows a transverse plane of a medical patient's skull, a CT slice 704 that shows a sagittal plane of the medical patient's skull, and a CT slice 706 that shows a coronal plane of the medical patient's skull. As also shown, FIG. 7 illustrates a perspective view 708 that shows how the CT slice 702, the CT slice 704, and the CT slice 706 (e.g., that shows how the transverse plane, the sagittal plane, and the coronal plane) intersect each other in three-dimensional space. As a non-limiting example that is for purposes of illustration, suppose that only such three principal anatomical planes were of concern. In such case, the set of principal anatomical plane localizations 306 could have a cardinality of three. For instance, a first principal anatomical plane localization of the set of principal anatomical plane localizations 306 could correspond to a transverse plane (e.g., could indicate/convey where the transverse plane is located in the 3D medical image 104 and/or could otherwise indicate/convey which voxels of the 3D medical image 104 make up the transverse plane). Moreover, a second principal anatomical plane localization of the set of principal anatomical plane localizations 306 could correspond to a sagittal plane (e.g., could indicate/convey where the sagittal plane is located in the 3D medical image 104 and/or could otherwise indicate/convey which voxels of the 3D medical image 104 make up the sagittal plane). Furthermore, a third principal anatomical plane localization of the set of principal anatomical plane localizations 306 could correspond to a coronal plane (e.g., could indicate/convey where the coronal plane is located in the 3D medical image 104 and/or could otherwise indicate/convey which voxels of the 3D medical image 104 make up the coronal plane). Those having ordinary skill in the art will appreciate that FIG. 7 is a mere non-limiting example for purposes of explanation.

Referring back to FIG. 4 once more, the set of organ segmentations 308 can include p segmentations for any suitable positive integer p: an organ segmentation 1 to an organ segmentation p. In various aspects, each organ segmentation can convey, indicate, identify, and/or otherwise represent a position and/or location of a respectively corresponding organ of the 3D medical image 104. For example, the organ segmentation 1 can be one or more scalars, one or more vectors, one or more matrices, one or more tensors, and/or one or more character strings that indicate which voxels of the 3D medical image 104 belong to and/or otherwise make up a first organ in the 3D medical image 104. In some cases, the organ segmentation 1 can be a voxel-wise mask indicating which voxels of the 3D medical image 104 are part of the first organ. Similarly, the organ segmentation p can be one or more scalars, one or more vectors, one or more matrices, one or more tensors, and/or one or more character strings that indicate which voxels of the 3D medical image 104 belong to and/or otherwise make up a p-th organ in the 3D medical image 104. Again, in some cases, the anatomical landmark localization p can be a voxel-wise mask indicating which voxels of the 3D medical image 104 are part of the p-th organ. As those having ordinary skill in the art will appreciate, an organ can be any suitable biological tissue and/or collection of biological tissues that can be considered as a constituent component of the anatomical structure depicted in the 3D medical image 104. Non-limiting examples of organs can include brain tissue, eye tissue, nasal tissue, bone tissue, tongue tissue, lung tissue, ear tissue, spinal tissue, and/or arterial tissue.

Although FIG. 4 illustrates the machine learning model 302 as generating all three of the set of anatomical landmark localizations 304, the set of principal anatomical plane localizations 306, and the set of organ segmentations 308, this is a mere non-limiting example. In various embodiments, the machine learning model 302 can comprise three separate machine learning models (e.g., three separate deep learning neural networks), each of which can be configured to generate a respective one of the set of anatomical landmark localizations 304, the set of principal anatomical plane localizations 306, and the set of organ segmentations 308. For example, there can be a first machine learning model that is configured to receive as input the 3D medical image 104 and that is configured to produce as output the set of anatomical landmark localizations 304, there can be a second machine learning model that is configured to receive as input the 3D medical image 104 and that is configured to produce as output the set of principal anatomical plane localizations 306, and there can be a third machine learning model that is configured to receive as input the 3D medical image 104 and that is configured to produce as output the set of organ segmentations 308. In any case, the set of anatomical landmark localizations 304, the set of principal anatomical plane localizations 306, and the set of organ segmentations 308 can all be generated via execution of deep learning on the 3D medical image 104.

Although FIG. 4 illustrates the machine learning model 302 as generating all three of the set of anatomical landmark localizations 304, the set of principal anatomical plane localizations 306, and the set of organ segmentations 308 in one shot, this is a mere non-limiting example. In various embodiments, the machine learning model 302 can comprise multiple machine learning models (e.g., multiple deep learning neural networks) that are hierarchically configured to perform progressively finer localizations and/or segmentations. For example, a first machine learning model can be configured to receive as input the 3D medical image 104 and that is configured to localize as output coarse/large/primary anatomical landmarks, coarse/large/primary anatomical planes, and/or coarse/large/primary organs that are depicted in the 3D medical image 104. Moreover, a second machine learning model can be configured to receive as input any suitable cropped volume of the 3D medical image 104 and can be configured to localize as output finer/smaller/secondary anatomical landmarks, finer/smaller/secondary anatomical planes, and/or finer/smaller/secondary organs that are depicted in the cropped volume of the 3D medical image 104. In various cases, any suitable number of progressively finer machine learning models can be implemented in this fashion as desired.

Figure 8:
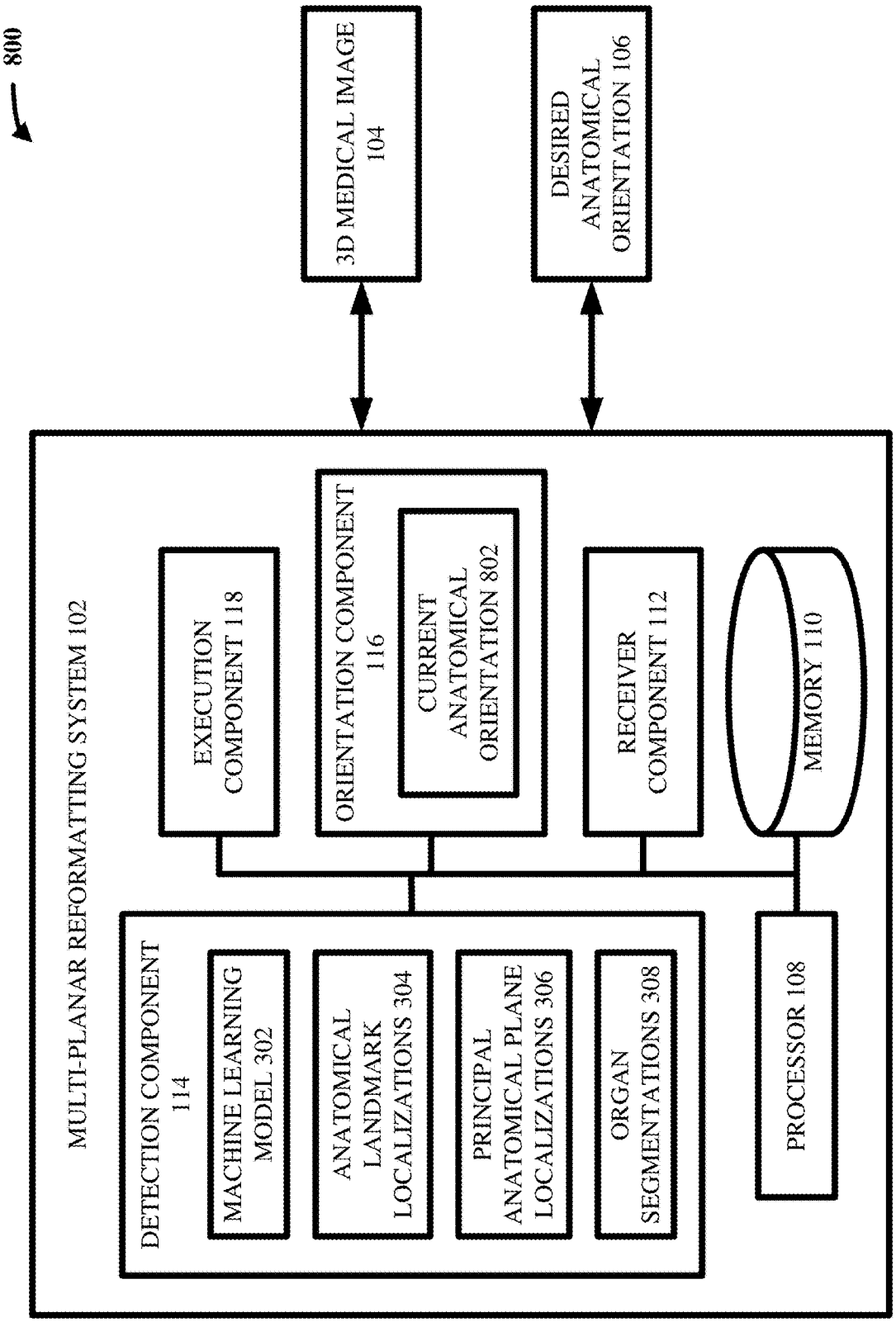
FIG. 8 illustrates a block diagram of an example, non-limiting system including a current anatomical orientation that facilitates deep learning multi-planar reformatting for medical images in accordance with one or more embodiments described herein.

FIG. 8 illustrates a block diagram of an example, non-limiting system 800 including a current anatomical orientation that can facilitate deep learning multi-planar reformatting for medical images in accordance with one or more embodiments described herein. As shown, the system 800 can, in some cases, comprise the same components as the system 300, and can further comprise a current anatomical orientation 802.

In various embodiments, the current anatomical orientation 802 can be one or more scalars, one or more vectors, one or more matrices, one or more tensors, and/or one or more character strings that conveys, indicates, and/or otherwise represents how the anatomical structure depicted in the 3D medical image 104 is currently oriented (e.g., prior to reformatting and/or reorientation by the multi-planar reformatting system 102). In various aspects, the orientation component 116 can electronically determine the current anatomical orientation 802 based on the set of anatomical landmark localizations 304, the set of principal anatomical plane localizations 306, and/or the set of organ segmentations 308. This is explained more with respect to FIG. 9.

Figure 9:
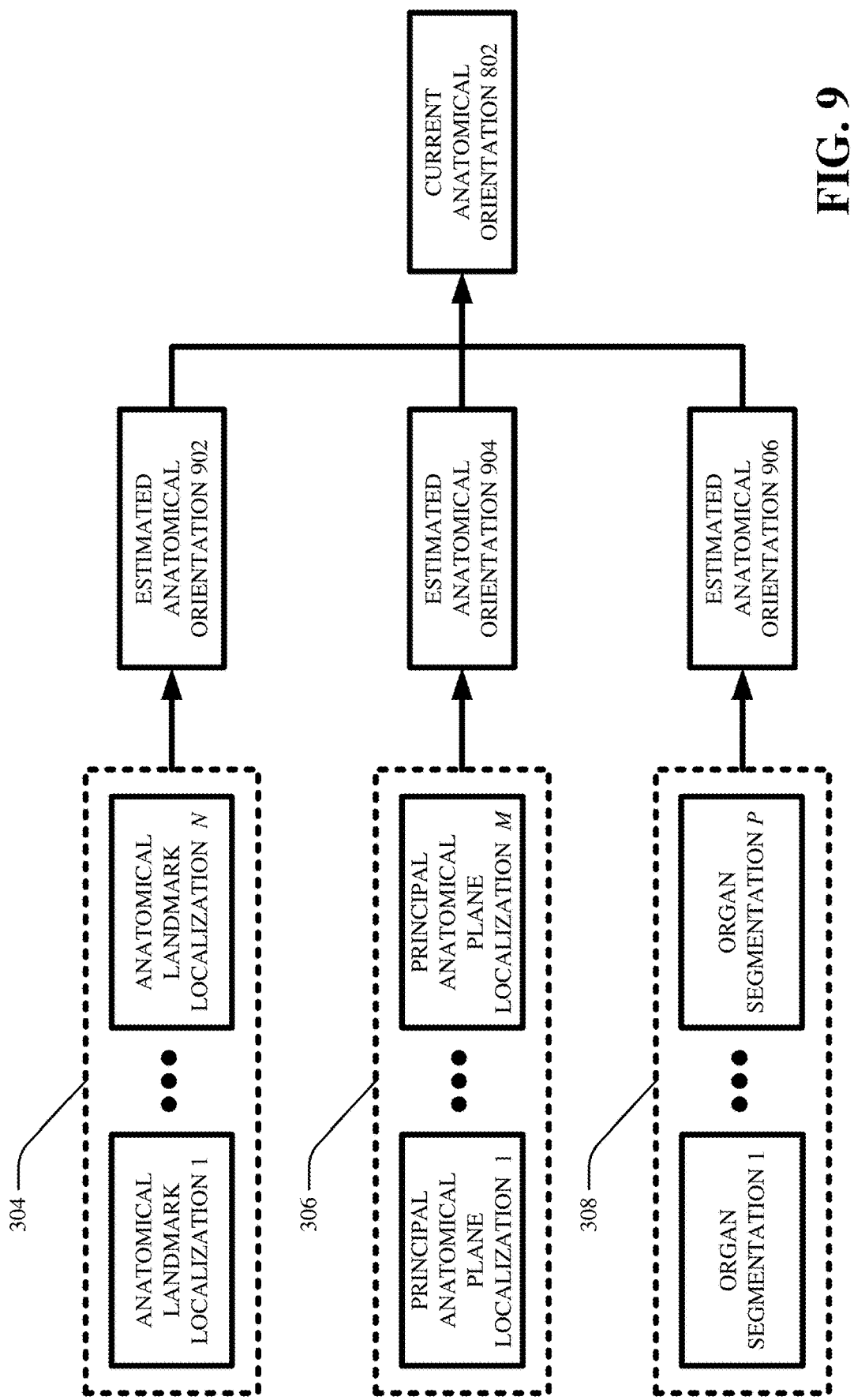
FIG. 9 illustrates an example, non-limiting block diagram showing how a current anatomical orientation can be computed based on a set of anatomical landmark localizations, a set of principal anatomical plane localizations, and/or a set of organ segmentations in accordance with one or more embodiments described herein.

FIG. 9 illustrates an example, non-limiting block diagram 900 showing how the current anatomical orientation 802 can be computed based on the set of anatomical landmark localizations 304, the set of principal anatomical plane localizations 306, and/or the set of organ segmentations 308 in accordance with one or more embodiments described herein.

As shown, in various aspects, the orientation component 116 can electronically calculate and/or compute an estimated anatomical orientation 902 based on the set of anatomical landmark localizations 304. In various instances, such calculation and/or computation can be facilitated via any suitable analytical techniques as desired. Indeed, as those having ordinary skill in the art will appreciate, the set of anatomical landmark localizations 304 can be considered as representing and/or conveying geometric relationships between various anatomical landmarks of the 3D medical image 104 (e.g., when the location and/or position of each anatomical landmark is known, the geometric distance between and/or the spatial arrangement of any given pair of anatomical landmarks can be computed). Those having ordinary skill in the art will appreciate how to calculate and/or compute (e.g., using any suitable geometric and/or trigonometric formulas) an anatomical orientation when given such geometric relationships of anatomical landmarks (e.g., a front-facing anatomical direction of a head can pass through a nasion landmark and can be perpendicular to and/or can bisect a line connecting a right-side external auditory canal landmark to a left-side external auditory canal landmark).

In any case, the orientation component 116 can electronically determine the estimated anatomical orientation 902 based on the set of anatomical landmark localizations 304. In various instances, the estimated anatomical orientation 902 can be one or more scalars, one or more vectors, one or more matrices, one or more tensors, and/or one or more character strings that conveys and/or otherwise represents a current orientation of the anatomical structure depicted in the 3D medical image 104. In various cases, the estimated anatomical orientation 902 can be based on the set of anatomical landmark localizations 304, as described above, and can be based on neither the set of principal anatomical plane localizations 306 nor the set of organ segmentations 308. Accordingly, if the set of anatomical landmark localizations 304 are correct (e.g., if the machine learning model 302 accurately localized the anatomical landmarks in the 3D medical image 104), then the estimated anatomical orientation 902 can be considered as correct (e.g., as accurately representing the orientation of the anatomical structure depicted in the 3D medical image 104), notwithstanding any inaccuracies in the set of principal anatomical plane localizations 306 and/or inaccuracies in the set of organ segmentations 308. In some cases, the estimated anatomical orientation 902 can thus be considered as a landmark-based estimation of the orientation of the anatomical structured depicted in the 3D medical image 104.

As further shown, in various aspects, the orientation component 116 can electronically calculate and/or compute an estimated anatomical orientation 904 based on the set of principal anatomical plane localizations 306. In various instances, such calculation and/or computation can be facilitated via any suitable analytical techniques as desired. Indeed, as those having ordinary skill in the art will appreciate, the set of principal anatomical plane localizations 306 can be considered as representing and/or conveying geometric relationships between various principal anatomical planes of the 3D medical image 104 (e.g., geometric position/location of transverse plane, geometric position/location of sagittal plane, geometric position/location of coronal plane). Those having ordinary skill in the art will appreciate how to calculate and/or compute (e.g., using any suitable geometric and/or trigonometric formulas) an anatomical orientation when given such geometric relationships of principal anatomical planes (e.g., a transverse plane can divide an anatomical structure into cranial and caudal portions, a sagittal plane can divide an anatomical structure into left and right portions, and a coronal plane can divide an anatomical structure into dorsal and ventral portions).

In any case, the orientation component 116 can electronically determine the estimated anatomical orientation 904 based on the set of principal anatomical plane localizations 306. In various instances, the estimated anatomical orientation 904 can be one or more scalars, one or more vectors, one or more matrices, one or more tensors, and/or one or more character strings that conveys and/or otherwise represents a current orientation of the anatomical structure depicted in the 3D medical image 104. In various cases, the estimated anatomical orientation 904 can be based on the set of principal anatomical plane localizations 306, as described above, and can be based on neither the set of anatomical landmark localizations 304 nor the set of organ segmentations 308. Accordingly, if the set of principal anatomical plane localizations 306 are correct (e.g., if the machine learning model 302 accurately localized the principal anatomical planes in the 3D medical image 104), then the estimated anatomical orientation 904 can be considered as correct (e.g., as accurately representing the orientation of the anatomical structure depicted in the 3D medical image 104), notwithstanding any inaccuracies in the set of anatomical landmark localizations 304 and/or inaccuracies in the set of organ segmentations 308. In some cases, the estimated anatomical orientation 904 can thus be considered as a plane-based estimation of the orientation of the anatomical structured depicted in the 3D medical image 104.

Moreover, in various aspects, the orientation component 116 can electronically calculate and/or compute an estimated anatomical orientation 906 based on the set of organ segmentations 308. In various instances, such calculation and/or computation can be facilitated via any suitable analytical techniques as desired. Indeed, as those having ordinary skill in the art will appreciate, the set of organ segmentations 308 can be considered as representing and/or conveying geometric relationships between various organs of the 3D medical image 104 (e.g., when the location and/or position of each organ is known, the geometric distance between and/or the spatial arrangement of any given pair of organs can be computed). Those having ordinary skill in the art will appreciate how to calculate and/or compute (e.g., using any suitable geometric and/or trigonometric formulas) an anatomical orientation when given such geometric relationships of organs (e.g., a front-facing anatomical direction of a head can pass away from brain tissue and toward eye tissue).

In any case, the orientation component 116 can electronically determine the estimated anatomical orientation 906 based on the set of organ segmentations 308. In various instances, the estimated anatomical orientation 906 can be one or more scalars, one or more vectors, one or more matrices, one or more tensors, and/or one or more character strings that conveys and/or otherwise represents a current orientation of the anatomical structure depicted in the 3D medical image 104. In various cases, the estimated anatomical orientation 906 can be based on the set of organ segmentations 308, as described above, and can be based on neither the set of anatomical landmark localizations 304 nor the set of principal anatomical plane localizations 306. Accordingly, if the set of organ segmentations 308 are correct (e.g., if the machine learning model 302 accurately segmented the organs in the 3D medical image 104), then the estimated anatomical orientation 906 can be considered as correct (e.g., as accurately representing the orientation of the anatomical structure depicted in the 3D medical image 104), notwithstanding any inaccuracies in the set of anatomical landmark localizations 304 and/or inaccuracies in the set of principal anatomical plane localizations 306. In some cases, the estimated anatomical orientation 906 can thus be considered as an organ-based estimation of the orientation of the anatomical structured depicted in the 3D medical image 104.

In various embodiments, the orientation component 116 can electronically aggregate the estimated anatomical orientation 902, the estimated anatomical orientation 904, and the estimated anatomical orientation 906 together, and the result of such aggregation can be considered as the current anatomical orientation 802. For example, in some cases, the orientation component 116 can electronically compute an average (e.g., weighted and/or unweighted) of the estimated anatomical orientation 902, the estimated anatomical orientation 904, and the estimated anatomical orientation 906, and the current anatomical orientation 802 can be equal to and/or otherwise based on such average.

Note that, if all three of the estimated anatomical orientation 902, the estimated anatomical orientation 904, and the estimated anatomical orientation 906 are accurate (e.g., if the machine learning model 302 accurately localized/segmented the landmarks, planes, and organs of the 3D medical image 104), then the current anatomical orientation 802 can likewise be considered as accurate (e.g., as correctly representing the actual orientation exhibited by the anatomical structure depicted in the 3D medical image 104). Moreover, note that, if any one of the estimated anatomical orientation 902, the estimated anatomical orientation 904, and the estimated anatomical orientation 906 is inaccurate, then the current anatomical orientation 802 can nevertheless be considered as sufficiently accurate, provided that the other two of the estimated anatomical orientation 902, the estimated anatomical orientation 904, and the estimated anatomical orientation 906 are accurate.

For example, if the estimated anatomical orientation 902 is inaccurate (e.g., if the machine learning model 302 inaccurately localized the anatomical landmarks of the 3D medical image 104), the current anatomical orientation 802 can nevertheless be considered as sufficiently accurate, provided that the estimated anatomical orientation 904 and the estimated anatomical orientation 906 are accurate (e.g., provided that the machine learning model 302 accurately localized/segmented the principal anatomical planes and organs of the 3D medical image 104). In other words, because the current anatomical orientation 802 can be an aggregation of the estimated anatomical orientation 902, the estimated anatomical orientation 904, and the estimated anatomical orientation 906, an inaccuracy in the estimated anatomical orientation 902 can be considered as being compensated for by accuracies in the estimated anatomical orientation 904 and the estimated anatomical orientation 906.

As another example, if the estimated anatomical orientation 904 is inaccurate (e.g., if the machine learning model 302 inaccurately localized the principal anatomical planes of the 3D medical image 104), the current anatomical orientation 802 can nevertheless be considered as sufficiently accurate, provided that the estimated anatomical orientation 902 and the estimated anatomical orientation 906 are accurate (e.g., provided that the machine learning model 302 accurately localized/segmented the anatomical landmarks and organs of the 3D medical image 104). In other words, because the current anatomical orientation 802 can be an aggregation of the estimated anatomical orientation 902, the estimated anatomical orientation 904, and the estimated anatomical orientation 906, an inaccuracy in the estimated anatomical orientation 904 can be considered as being compensated for by accuracies in the estimated anatomical orientation 902 and the estimated anatomical orientation 906.

As still another example, if the estimated anatomical orientation 906 is inaccurate (e.g., if the machine learning model 302 inaccurately segmented the organs of the 3D medical image 104), the current anatomical orientation 802 can nevertheless be considered as sufficiently accurate, provided that the estimated anatomical orientation 902 and the estimated anatomical orientation 904 are accurate (e.g., provided that the machine learning model 302 accurately localized the anatomical landmarks and principal anatomical planes of the 3D medical image 104). In other words, because the current anatomical orientation 802 can be an aggregation of the estimated anatomical orientation 902, the estimated anatomical orientation 904, and the estimated anatomical orientation 906, an inaccuracy in the estimated anatomical orientation 906 can be considered as being compensated for by accuracies in the estimated anatomical orientation 902 and the estimated anatomical orientation 904.

Although the herein disclosure mainly describes various embodiments of the subject innovation as applying analytical techniques to generate the estimated anatomical orientation 902, the estimated anatomical orientation 904, and/or the estimated anatomical orientation 906, this is a mere non-limiting example. In some embodiments, any suitable deep learning techniques can be implemented to generate such estimated orientations as desired (e.g., a first deep learning model can be configured/trained to receive as input the set of anatomical landmark localizations 304 and to produce as output the estimated anatomical orientation 902; a second deep learning model can be configured/trained to receive as input the set of principal anatomical plane localizations 306 and to produce as output the estimated anatomical orientation 904; a third deep learning model can be configured/trained to receive as input the set of organ segmentations 308 and to produce as output the estimated anatomical orientation 906). Indeed, in some cases, a deep learning model can be configured to receive as input all three of the set of anatomical landmark localizations 304, the set of principal anatomical plane localizations 306, and the set of organ segmentations 308, and to produce as output the current anatomical orientation 802.

In any case, the orientation component 116 can electronically determine the current anatomical orientation 802, based on the set of anatomical landmark localizations 304, the set of principal anatomical plane localizations 306, and/or the set of organ segmentations 308.

In various embodiments, the execution component 118 can electronically rotate, translate, manipulate, reformat, and/or otherwise reorient the 3D medical image 104 based on the current anatomical orientation 802, such that the anatomical structure depicted in the 3D medical image 104 now exhibits the desired anatomical orientation 106. Those having ordinary skill in the art will appreciate that, when given two different orientations of an anatomical structure, a mathematical transformation (e.g., one or more shifts and/or rotations) can be computed so as to transform one of such orientations into the other. In this way, once the orientation component 116 estimates/determines the current anatomical orientation 802, the execution component 118 can estimate/determine the axes about which and/or the angular sweeps by which the 3D medical image 104 should be rotated, so that the anatomical structure depicted in the 3D medical image 104 exhibits the desired anatomical orientation 106. In various cases, the execution component 118 can electronically transmit the 3D medical image 104, after such rotation/reorientation, to any suitable computing device (not shown) as desired. In various other cases, the execution component 118 can electronically render, on any suitable computer screen/monitor (not shown), the 3D medical image 104 and/or any cross-sections thereof after such rotation/reorientation.

Although various embodiments have been described as localizing and/or segmenting all of the landmarks, principal planes, and/or organs of the 3D medical image 104 prior to reorienting/rotating the 3D medical image 104, this is a mere non-limiting example. In some embodiments, multiple segmentation-reorientation passes of the 3D medical image 104 can be collectively performed by the detection component 114, the orientation component 116, and the execution component 118, where each pass involves segmenting and/or reorienting a progressively finer portion of the 3D medical image 104. For example, suppose that the 3D medical image 104 depicts a patient's head. In such case, the detection component 114, the orientation component 116, and the execution component 118 can perform a first, coarse pass on the 3D medical image 104: that is, the detection component 114 can execute the machine learning model 302 on the 3D medical image 104, thereby yielding coarse anatomical landmark localizations for the patient's head, coarse principal anatomical plane localizations for the patient's head, and coarse organ segmentations for the patient's head, the orientation component 116 can determine the current orientation of the patient's head based on such output, and the execution component 118 can rotate the 3D medical image 104 accordingly. Next, the detection component 114, the orientation component 116, and the execution component 118 can perform a second, finer pass on the 3D medical image 104: that is, the detection component 114 can execute the machine learning model 302 on a finer and/or smaller portion of the 3D medical image 104 (e.g., a cropped portion showing the sinuses of the medical patient), thereby yielding finer anatomical landmark localizations for the patient's head (e.g., landmarks specific to the patient's sinuses), finer principal anatomical plane localizations for the patient's head (e.g., planes specific to the patient's sinuses), and finer organ segmentations for the patient's head (e.g., organs specific to the patient's sinuses), the orientation component 116 can update the current orientation of the patient's head based on such output, and the execution component 118 can re-rotate the 3D medical image 104 accordingly. In this way, progressively finer localizations, segmentations, and/or reorientations can be performed. Those having ordinary skill in the art will appreciate that any suitable number of such progressively finer passes can be implemented as desired.

As described above, the machine learning model 302 can be configured to receive as input the 3D medical image 104, and to produce as output the set of anatomical landmark localizations 304, the set of principal anatomical plane localizations 306, and the set of organ segmentations 308. In order to facilitate such functionality, the machine learning model 302 should first be trained. In various cases, the machine learning model 302 can be trained in supervised fashion, as described with respect to FIGS. 10-12.

Figure 10:
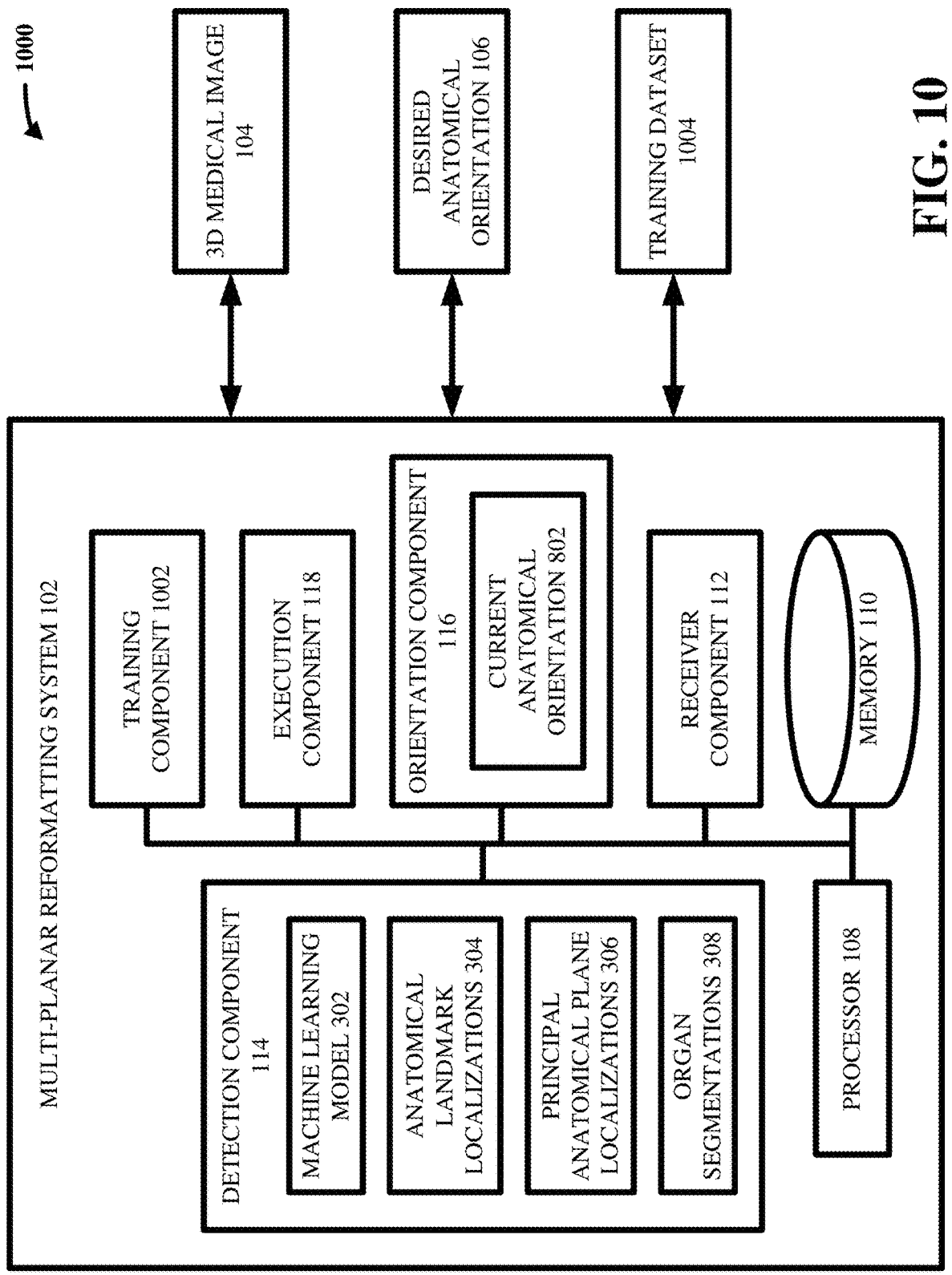
FIG. 10 illustrates a block diagram of an example, non-limiting system including a training component and/or a training dataset that facilitates deep learning multi-planar reformatting for medical images in accordance with one or more embodiments described herein.

FIG. 10 illustrates a block diagram of an example, non-limiting system 1000 including a training component and/or a training dataset that can facilitate deep learning multi-planar reformatting for medical images in accordance with one or more embodiments described herein. As shown, the system 1000 can, in some cases, comprise the same components as the system 800, and can further comprise a training component 1002 and/or a training dataset 1004.

Figure 11:
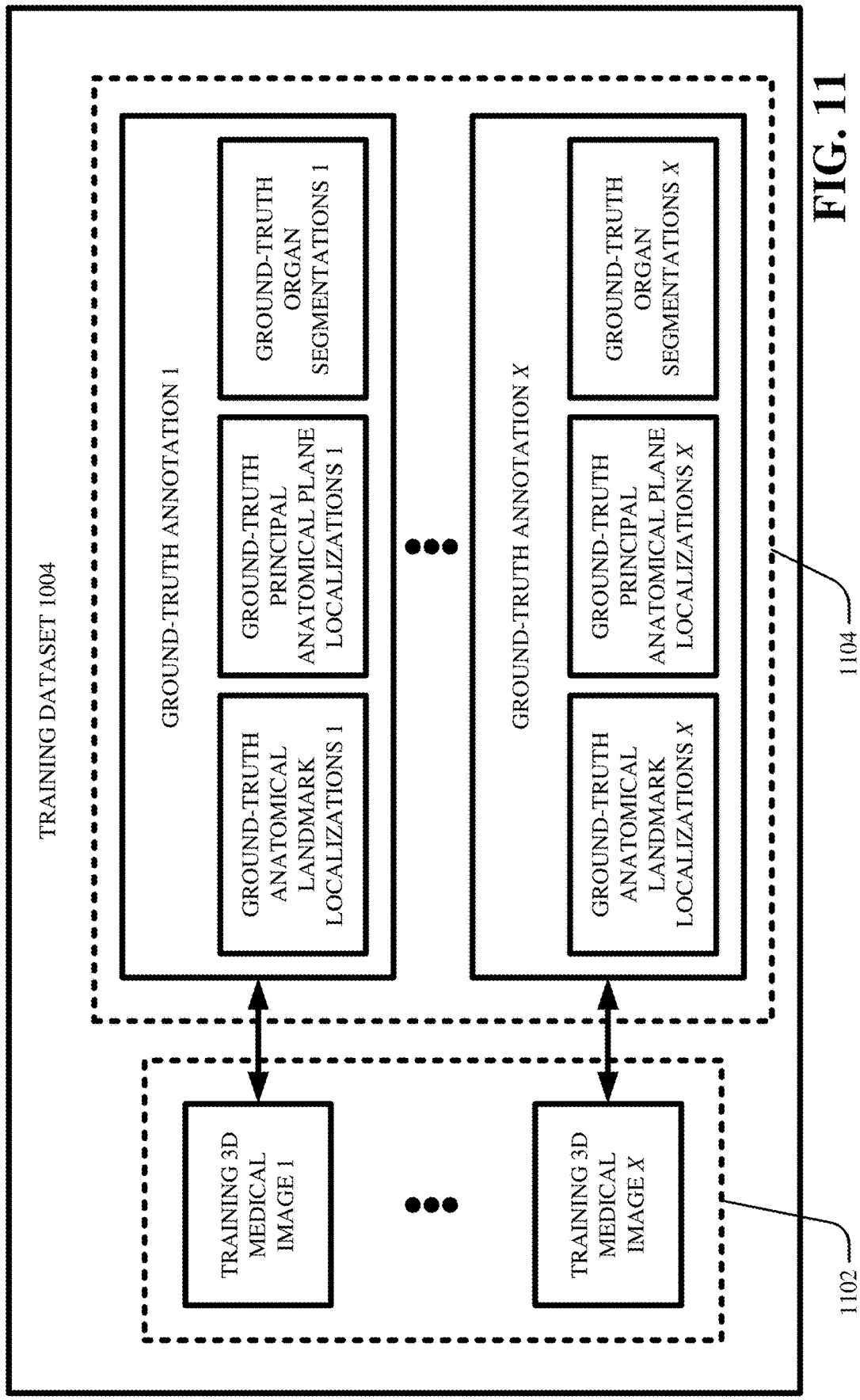
FIG. 11 illustrates an example, non-limiting block diagram of a training dataset in accordance with one or more embodiments described herein.
Figure 12:
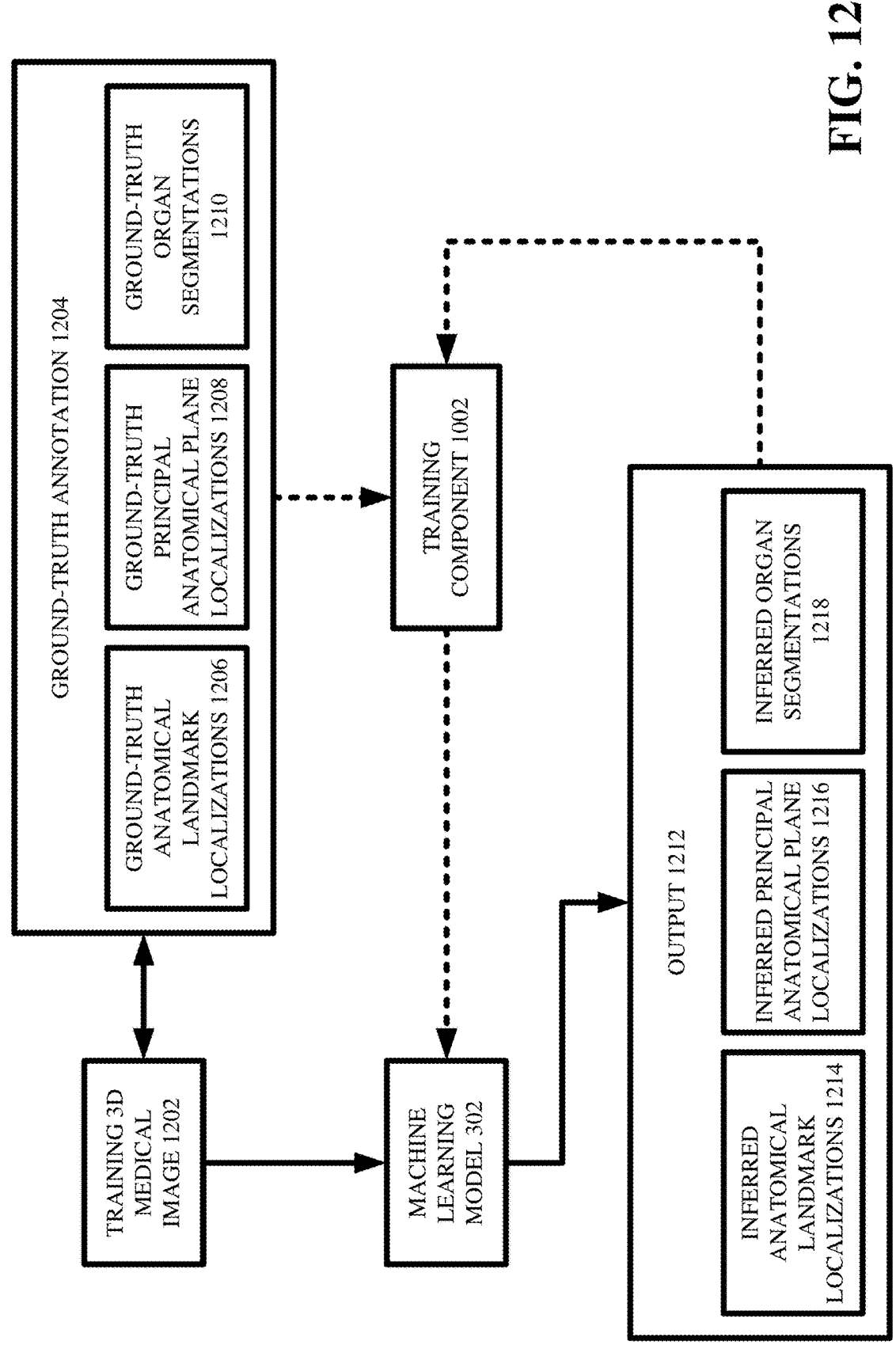
FIG. 12 illustrates an example, non-limiting block diagram showing how a machine learning model can be trained on a training dataset in accordance with one or more embodiments described herein.

In various embodiments, the receiver component 112 can electronically receive, retrieve, and/or otherwise access, from any suitable source, the training dataset 1004, and the training component 1002 can electronically train the machine learning model 302 on the training dataset 1004, as described with respect to FIGS. 11-12.

FIG. 11 illustrates an example, non-limiting block diagram 1100 of a training dataset in accordance with one or more embodiments described herein. That is, FIG. 11 depicts a non-limiting example embodiment of the training dataset 1004.

In various aspects, the training dataset 1004 can include a set of training 3D medical images 1102 and/or a set of ground-truth annotations 1104. In various instances, the set of training 3D medical images 1102 can include x images for any suitable positive integer x: a training 3D medical image 1 to a training 3D medical image x. In various cases, each of the set of training 3D medical images 1102 can have the same format and/or dimensionality (e.g., can have the same number and/or arrangement of voxels) as the 3D medical image 104. In various aspects, the set of ground-truth annotations 1104 can respectively correspond in one-to-one fashion to the set of training 3D medical images 1102. Accordingly, the set of ground-truth annotations 1104 can include x annotations: a ground-truth annotation 1 to a ground-truth annotation x, where the ground-truth annotation 1 corresponds to the training 3D medical image 1, and where the ground-truth annotation x corresponds to the training 3D medical image x. In various cases, each of the set of ground-truth annotations 1104 can include a set of ground-truth anatomical landmark localizations, a set of ground-truth principal anatomical plane localizations, and/or a set of ground-truth organ segmentations. In various instances, each set of ground-truth anatomical landmark localizations can have the same format and/or dimensionality as the set of anatomical landmark localizations 304, each set of ground-truth principal anatomical plane localizations can have the same format and/or dimensionality as the set of principal anatomical plane localizations 306, and/or each set of ground-truth organ segmentations can have the same format and/or dimensionality as the set of organ segmentations 308.

For example, the ground-truth annotation 1 can include a set of ground-truth anatomical landmark localizations 1, a set of ground-truth principal anatomical plane localizations 1, and/or a set of ground-truth organ segmentations 1. Since the ground-truth annotation 1 can correspond to the training 3D medical image 1, the set of ground-truth anatomical landmark localizations 1 can be considered as conveying, indicating, and/or otherwise representing the correct/accurate anatomical landmarks that are known and/or deemed to be depicted in the training 3D image 1 (e.g., can be considered as indicating which voxels of the training 3D medical image 1 are known/deemed to belong to which anatomical landmarks). Moreover, since the ground-truth annotation 1 can correspond to the training 3D medical image 1, the set of ground-truth principal anatomical plane localizations 1 can be considered as conveying, indicating, and/or otherwise representing the correct/accurate principal anatomical planes that are known and/or deemed to be depicted in the training 3D image 1 (e.g., can be considered as indicating which voxels of the training 3D medical image 1 are known/deemed to belong to which principal anatomical planes). Furthermore, since the ground-truth annotation 1 can correspond to the training 3D medical image 1, the set of ground-truth organ segmentations 1 can be considered as conveying, indicating, and/or otherwise representing the correct/accurate organs that are known and/or deemed to be depicted in the training 3D image 1 (e.g., can be considered as indicating which voxels of the training 3D medical image 1 are known/deemed to belong to which organs).

As another example, the ground-truth annotation x can include a set of ground-truth anatomical landmark localizations x, a set of ground-truth principal anatomical plane localizations x, and/or a set of ground-truth organ segmentations x. Since the ground-truth annotation x can correspond to the training 3D medical image x, the set of ground-truth anatomical landmark localizations x can be considered as conveying, indicating, and/or otherwise representing the correct/accurate anatomical landmarks that are known and/or deemed to be depicted in the training 3D image x (e.g., can be considered as indicating which voxels of the training 3D medical image x are known/deemed to belong to which anatomical landmarks). Moreover, since the ground-truth annotation x can correspond to the training 3D medical image x, the set of ground-truth principal anatomical plane localizations x can be considered as conveying, indicating, and/or otherwise representing the correct/accurate principal anatomical planes that are known and/or deemed to be depicted in the training 3D image x (e.g., can be considered as indicating which voxels of the training 3D medical image x are known/deemed to belong to which principal anatomical planes). Further still, since the ground-truth annotation x can correspond to the training 3D medical image x, the set of ground-truth organ segmentations x can be considered as conveying, indicating, and/or otherwise representing the correct/accurate organs that are known and/or deemed to be depicted in the training 3D image x (e.g., can be considered as indicating which voxels of the training 3D medical image x are known/deemed to belong to which organs).

FIG. 12 illustrates an example, non-limiting block diagram 1200 showing how the machine learning model 302 can be trained on the training dataset 1004 in accordance with one or more embodiments described herein.

In various embodiments, the internal parameters (e.g., weights, biases) of the machine learning model 302 can be randomly initialized (and/or initialized in any other suitable fashion). In various aspects, the training component 1002 can electronically select a training 3D medical image 1202 from the training dataset 1004. As shown, the training 3D medical image 1202 can correspond to a ground-truth annotation 1204, which can include a set of ground-truth anatomical landmark localizations 1206, a set of ground-truth principal anatomical plane localizations 1208, and/or a set of ground-truth organ segmentations 1210. In various instances, the training component 1002 can electronically feed the 3D medical image 1202 as input to the machine learning model 302, and this can cause the machine learning model 302 to produce some output 1212. More specifically, an input layer of the machine learning model 302 can receive the training 3D medical image 1202, the training 3D medical image 1202 can complete a forward pass through one or more hidden layers of the machine learning model 302, and an output layer of the machine learning model 302 can generate and/or compute the output 1212 based on activations yielded by the one or more hidden layers.

As shown, the output 1212 can include a set of inferred anatomical landmark localizations 1214, a set of inferred principal anatomical plane localizations 1216, and/or a set of inferred organ segmentations 1218. In various aspects, the set of inferred anatomical landmark localizations 1214 can be considered as representing the anatomical landmarks which the machine learning model 302 believes and/or infers are depicted in the training 3D medical image 1202, whereas the set of ground-truth anatomical landmark localizations 1206 can be considered as representing the correct/accurate anatomical landmarks that are known and/or deemed to be depicted in the training 3D medical image 1202. Similarly, the set of inferred principal anatomical plane localizations 1216 can be considered as representing the principal anatomical planes which the machine learning model 302 believes and/or infers are depicted in the training 3D medical image 1202, whereas the set of ground-truth anatomical landmark localizations 1206 can be considered as representing the correct/accurate principal anatomical planes that are known and/or deemed to be depicted in the training 3D medical image 1202. Likewise, the set of inferred organ segmentations 1218 can be considered as representing the organs which the machine learning model 302 believes and/or infers are depicted in the training 3D medical image 1202, whereas the set of ground-truth organ segmentations 1210 can be considered as representing the correct/accurate organs that are known and/or deemed to be depicted in the training 3D medical image 1202. Note that, if the machine learning model 302 has so far undergone no and/or little training, then the output 1212 can be highly inaccurate (e.g., the set of inferred anatomical landmark localizations 1214 can be very different from the set of ground-truth anatomical landmark localizations 1206; the set of inferred principal anatomical plane localizations 1216 can be very different from the set of ground-truth principal anatomical plane localizations 1208; and/or the set of inferred organ segmentations 1218 can be very different from the set of ground-truth organ segmentations 1210).

In any case, the training component 1002 can electronically compute an error/loss between the output 1212 and the ground-truth annotation 1204. More specifically, in various aspects, the training component 1002 can compute a first preliminary error/loss between the set of inferred anatomical landmark localizations 1214 and the set of ground-truth anatomical landmark localizations 1206, the training component 1002 can compute a second preliminary error/loss between the set of inferred principal anatomical plane localizations 1216 and the set of ground-truth principal anatomical plane localizations 1208, and/or the training component 1002 can compute a third preliminary error/loss between the set of inferred organ segmentations 1218 and the set of ground-truth organ segmentations 1210. In such case, the training component 1002 can aggregate (e.g., add together) such three preliminary errors/losses, thereby yielding an overall error/loss. In any case, the training component 1002 can update, via backpropagation, the internal parameters of the machine learning model 302 based on such overall error/loss. Those having ordinary skill in the art will appreciate that, in some cases, the training component 1002 can perform backpropagation via gradient descent, whereas in other cases, the training component 1002 can perform backpropagation via gradient ascent, as appropriate.

In various aspects, the training component 1002 can repeat the above training procedure for each training 3D medical image in the training dataset 1004, with the ultimate result being that the internal parameters of the machine learning model 302 become iteratively optimized for accurately localizing and/or segmenting anatomical landmarks, principal anatomical planes, and/or organs in inputted medical image volumes. Those having ordinary skill in the art will appreciate that any suitable training batch sizes, any suitable training termination criteria, and/or any suitable error/loss functions can be implemented as desired.

As mentioned above, the training component 1002 can, in some cases, compute a first preliminary error/loss between the set of inferred anatomical landmark localizations 1214 and the set of ground-truth anatomical landmark localizations 1206. A non-limiting example of such a first preliminary error/loss is described as follows.

When given a set of anatomical landmarks, such set of anatomical landmarks can be considered as forming a graph of nodes and edges, where each node can be and/or represent an anatomical landmark (e.g., geometric coordinates of the anatomical landmark), and where each edge can be and/or represent a spatial vector physically separating two nodes (e.g., can represent the geometric distance and/or direction between two anatomical landmarks). In some cases, an edge (i,j) of such graph can connect a node i to a node j. In various instances, the edge (i,j) can be vectorially represented as $\vec{d_{i,j}}$, and thus the length of the edge (i,j) can be represented as $|\vec{d_{i,j}}|$.

For any given edge (i,j), there can be a pre-defined ordered set $C_1$ of other edges in the graph to which the edge (i,j) can be compared. In various cases, the pre-defined ordered set $C_1$ can include any suitable number of other edges as desired. In various aspects, a distance comparison function $\varphi_{(i,j)} = \{f_{(i,j),(i',j')}|_{(i',j') \in C_1}\}$ can be defined as a set of distance-based relations between the edge (i,j) and each edge in $C_1$. As a non-limiting example, $\varphi_{(i,j)}$ can be given as follows:

$$\varphi_{(i,j)} = \{f(\vec{d_{i,j}}, \vec{d_{i',j'}})\}_{(i',j') \in C_1} = \left\{\frac{|\vec{d_{i,j}}|}{|\vec{d_{i',j'}}|}\right\}_{(i',j') \in C_1}$$

which can be considered as a set of ratios of distances between edges of the graph. For sake of notational efficiency, the edge (i,j) can be denoted as an edge k, and the edge (i',j') can be denoted as an edge k'. Accordingly, in various cases, the distance comparison function can be denoted as follows:

$$\varphi_k = \{f(\vec{d_k}, \vec{d_{k'}})\}_{k' \in C_1} = \left\{\frac{|\vec{d_k}|}{|\vec{d_{k'}}|}\right\}_{k' \in C_1}$$

Similarly, for any given edge (i, j), there can be a pre-defined ordered set $C_2$ of other edges in the graph to which the edge (i,j) can be compared. In various cases, the pre-defined ordered set $C_2$ can include any suitable number of other edges as desired. In some cases, the pre-defined ordered set $C_2$ can be the same as and/or different from the pre-defined ordered set $C_1$. In various aspects, an angular comparison function $\theta_{(i,j)} = \{f_{(i,j),(i',j')}|_{(i',j') \in C_2}\}$ can be defined as a set of angle-based relations between the edge (i,j) and each edge in $C_2$. As a non-limiting example, $\theta_{(i, j)}$ can be given as follows:

$$\theta_{i,j} = \{f(\vec{d_{i,j}}, \vec{d_{i',j'}})\}_{(i',j') \in C_2} = \left\{\cos^{-1}\frac{\vec{d_{i,j}} \cdot \vec{d_{i',j'}}}{|\vec{d_{i,j}}| \times |\vec{d_{i',j'}}|}\right\}_{(i',j') \in C_2}$$

which can be considered as a set of angles between edges of the graph. For sake of notational efficiency, the edge (i,j) can be denoted as an edge h, and the edge (i', j') can be denoted as an edge h'. Accordingly, in various cases, the angular comparison function can be denoted as follows:

$$\theta_m = \{f(\vec{d_h}, \vec{d_{h'}})\}_{h' \in C_2} = \left\{\cos^{-1}\frac{\vec{d_h} \cdot \vec{d_{h'}}}{|\vec{d_h}| \times |\vec{d_{h'}}|}\right\}_{h' \in C_2}$$

Thus far, edge characteristics have been discussed. However, in various aspects, node characteristics can be taken into account, as well. In such case, for any given node i of the graph (e.g., for any given anatomical landmark i), a set of characteristics $\psi_i = \{I_i, \nabla_i, T_i\}$ can be defined, where $I_i$ can represent an intensity level (e.g., Hounsfield unit) of the node i, where $\nabla I_i$ can represent an intensity gradient associated with the node i, and/or where $T_i$ can represent a texture associated with the node i. Those having ordinary skill in the art will appreciate that these are mere non-limiting examples of node/landmark characteristics and that any other suitable node/landmark characteristics can be implemented as desired.

Note how the various edge characteristics and node characteristics that have been discussed so far can be computed when given a set of anatomical landmark localizations. Therefore, such edge characteristics and node characteristics can be computed for the set of ground-truth anatomical landmark localizations 1206, and such edge characteristics and node characteristics can also be computed for the set of inferred anatomical landmark localizations 1214 (e.g., two different graphs can be created, one based on the set of ground-truth anatomical landmark localizations 1206 and another based on the set of inferred anatomical landmark localizations 1214).

Now, in various cases, a landmark edge loss $\mathcal{L}_{landmark\ edge}$ can be computed as follows:

$$\mathcal{L}_{landmark\ edge} = \alpha_1\left(\frac{1}{|K|}\sum_{k\in K}|\phi_k^{truth} - \phi_k^{pred}|\right) + \alpha_2\left(\frac{1}{|H|}\sum_{h\in H}|\theta_h^{truth} - \theta_h^{pred}|\right)$$

where K can be the set of graph edges on which it is desired to execute the distance comparison function $\phi$ (e.g., K can be equal to or lesser than the total number of graph edges), where $\phi_k^{truth}$ can be the result of applying the distance comparison function $\phi$ to a k-th edge of a graph that is computed based on the set of ground-truth anatomical landmark localizations 1206, where $\phi_k^{pred}$ can be the result of applying the distance comparison function $\phi$ to a k-th edge of a graph that is computed based on the set of inferred anatomical landmark localizations 1214, where $\alpha_1$ can be any suitable scalar, where H can be the set of graph edges on which it is desired to execute the angular comparison function $\theta$ (e.g., H can be equal to or lesser than the total number of graph edges), where $\theta_h^{pred}$ can be the result of applying the angular comparison function $\theta$ to an h-th edge of a graph that is computed based on the set of ground-truth anatomical landmark localizations 1206, where $\theta_h^{pred}$ can be the result of applying the angular comparison function $\theta$ to an h-th edge of a graph that is computed based on the set of inferred anatomical landmark localizations 1214, and where $\alpha_2$ can be any suitable scalar.

Moreover, a landmark node loss $\mathcal{L}_{landmark\ node}$ can be computed as follows:

$$\mathcal{L}_{landmark\ node} = \frac{1}{|R|}\sum_{r\in R}|\psi_r^{truth} - \psi_r^{pred}|^z$$

where R can be the set of graph nodes on which it is desired to compare node characteristics (e.g., R can be equal to or lesser than the total number of graph nodes), where $\psi_r^{truth}$ can be the characteristics of an r-th node of a graph that is computed based on the set of ground-truth anatomical landmark localizations 1206, where $\psi_r^{pred}$ can be the characteristics of an r-th node of a graph that is computed based on the set of inferred anatomical landmark localizations 1214, and/or where z can be any suitable scalar.

Furthermore, a landmark graph loss $\mathcal{L}_{landmark\ graph}$ can be computed as follows:

$$\mathcal{L}_{landmark\ graph} = \lambda_{landmark\ edge}\mathcal{L}_{landmark\ edge} + \lambda_{landmark\ node}\mathcal{L}_{landmark\ node}$$

where $\lambda_{landmark\ edge}$ can be any suitable scalar as desired, and/or where $\lambda_{landmark\ node}$ can be any suitable scalar as desired.

Further still, a global landmark loss $\mathcal{L}_{landmark\ global}$ can be computed be computed as follows:

$$\mathcal{L}_{landmark\ global} = \frac{\sum_{i=1}^{S}p_{io}\times g_{io} + \epsilon}{\sum_{i=1}^{S}p_{io}\times g_{io} + \alpha\sum_{i=1}^{S}p_{i\bar{o}}\times g_{io} + \beta\sum_{i=1}^{S}p_{io}\times g_{i\bar{o}} + \epsilon}$$

where S can be the total number of voxels in the 3D medical image 104, where o can represent an anatomical landmark class, where ō can represent a background class (e.g., a non-landmark class), where p can represent a predicted/inferred classification for a given voxel generated by the machine learning model 302, where g can represent a ground-truth landmark classification for a given voxel, and/or where $\alpha$, $\beta$, and $\epsilon$ can be any suitable scalars. Those having ordinary skill in the art will appreciate that $\mathcal{L}_{landmark\ global}$ can be considered as being equivalent to and/or otherwise based on a version of Tversky loss, Dice score coefficient, and/or Jaccard loss. That is, those having ordinary skill in the art will appreciate that $$\sum_{i=1}^{S}p_{io}\times g_{io}$$

represents number of true positives produced by the machine learning model 302, that $$\sum_{i=1}^{S}p_{i\bar{o}}\times g_{io}$$

represents number of false negatives produced by the machine learning model 302, and/or that $$\sum_{i=1}^{S}p_{io}\times g_{i\bar{o}}$$

represents number of false positives produced by the machine learning model 302.

Therefore, an overall landmark loss $\mathcal{L}_{landmark\ overall}$ can be computed as follows:

$$\mathcal{L}_{landmark\ overall} = \lambda_{landmark\ global}\mathcal{L}_{landmark\ global} + \lambda_{landmark\ graph}\mathcal{L}_{landmark\ graph}$$

where $\lambda_{landmark\ global}$ can be any suitable scalar as desired, and/or where $\lambda_{landmark\ graph}$ can be any suitable scalar as desired. In various aspects, $\mathcal{L}_{landmark\ overall}$ can be considered as the first preliminary error/loss mentioned above.

As mentioned above, the training component 1002 can, in some cases, compute a second preliminary error/loss between the set of inferred principal anatomical plane localizations 1216 and the set of ground-truth principal anatomical plane localizations 1208. A non-limiting example of such a second preliminary error/loss is described as follows.

In various aspects, content loss for a u-th principal anatomical plane can be given as follows:

$$\mathcal{L}_{plane\ content}^{u} = \frac{2*\left(\sum_{i=1}^{S}p_{ui}\times g_{ui}\right)}{\sum_{i=1}^{S}p_{ui} + \sum_{i=1}^{S}g_{ui} + \epsilon} + \frac{1}{S}\|I(p_u) - I(g_u)\|$$

where $p_u$ can be the set of voxels corresponding to the u-th plane in predicted output (e.g., as indicated by the set of inferred principal anatomical plane localizations 1216), where $g_u$ can be the set of voxels corresponding to the u-th plane in ground-truth output (e.g., as indicated by the set of ground-truth principal anatomical plane localizations 1208), where $I(p_u)$ can be the intensity values of the set of voxels corresponding to the u-th plane in predicted output (e.g., again, as indicated by the set of inferred principal anatomical plane localizations 1216), where $I(g_u)$ can be the intensity values of the set of voxels corresponding to the u-th plane in ground-truth output (e.g., again, as indicated by the set of ground-truth principal anatomical plane localizations 1208), and where £ can be any suitable scalar. Moreover, in various instances, total loss for the u-th principal anatomical plane can be given as follows:

$$\mathcal{L}_{plane\ total}{}^u = \lambda \mathcal{L}_{plane\ content}{}^u + (1-\lambda)\mathcal{L}_{adv}{}^u$$

where $\mathcal{L}_{adv}{}^u$ can be an adversarial loss, and where λ can be any suitable scalar. In various aspects, $$\sum_u \mathcal{L}^u_{plane\ total}$$

can be considered as the second preliminary error/loss mentioned above (e.g., summed across all the localized principal anatomical planes).

Lastly, as mentioned above, the training component 1002 can, in some cases, compute a third preliminary error/loss between the set of inferred organ segmentations 1218 and the set of ground-truth organ segmentations 1210. A non-limiting example of such a third preliminary error/loss is described as follows.

In various instances, a Dice similarity coefficient for any v-th organ can be given as follows:

$$\mathcal{L}^v_{Dice\ organ} = \frac{2*\left(\sum_{i=1}^S p_{vi} \times g_{vi}\right)}{\sum_{i=1}^S p_{vi} + \sum_{i=1}^S g_{vi} + \epsilon}$$

where $p_v$ can be the set of voxels corresponding to the v-th organ in predicted output (e.g., as indicated by the set of inferred organ segmentations 1218), where gv can be the set of voxels corresponding to the v-th organ in ground-truth output (e.g., as indicated by the set of ground-truth organ segmentations 1210), and where £ can be any suitable scalar. In various aspects, $$\sum_v \mathcal{L}^v_{Dice\ organ}$$

can be considered as the third preliminary error/loss mentioned above (e.g., summed across all the segmented organs).

Accordingly, in some cases, the first preliminary loss (e.g., landmark-based), the second preliminary loss (e.g., plane-based), and the third preliminary loss (e.g., organ-based) can be blended together in any suitable fashion, and such blended output can be considered as the total and/or overall loss with which the training component 1002 can perform backpropagation of the machine learning model 302.

Although FIGS. 10-12 mainly pertain to embodiments where the training component 1002 performs supervised training on the machine learning model 302, this is a mere non-limiting example. In various other embodiments, the training component 1002 can perform any other suitable type of training on the machine learning model 302 (e.g., unsupervised training, reinforcement learning).

Figure 13:
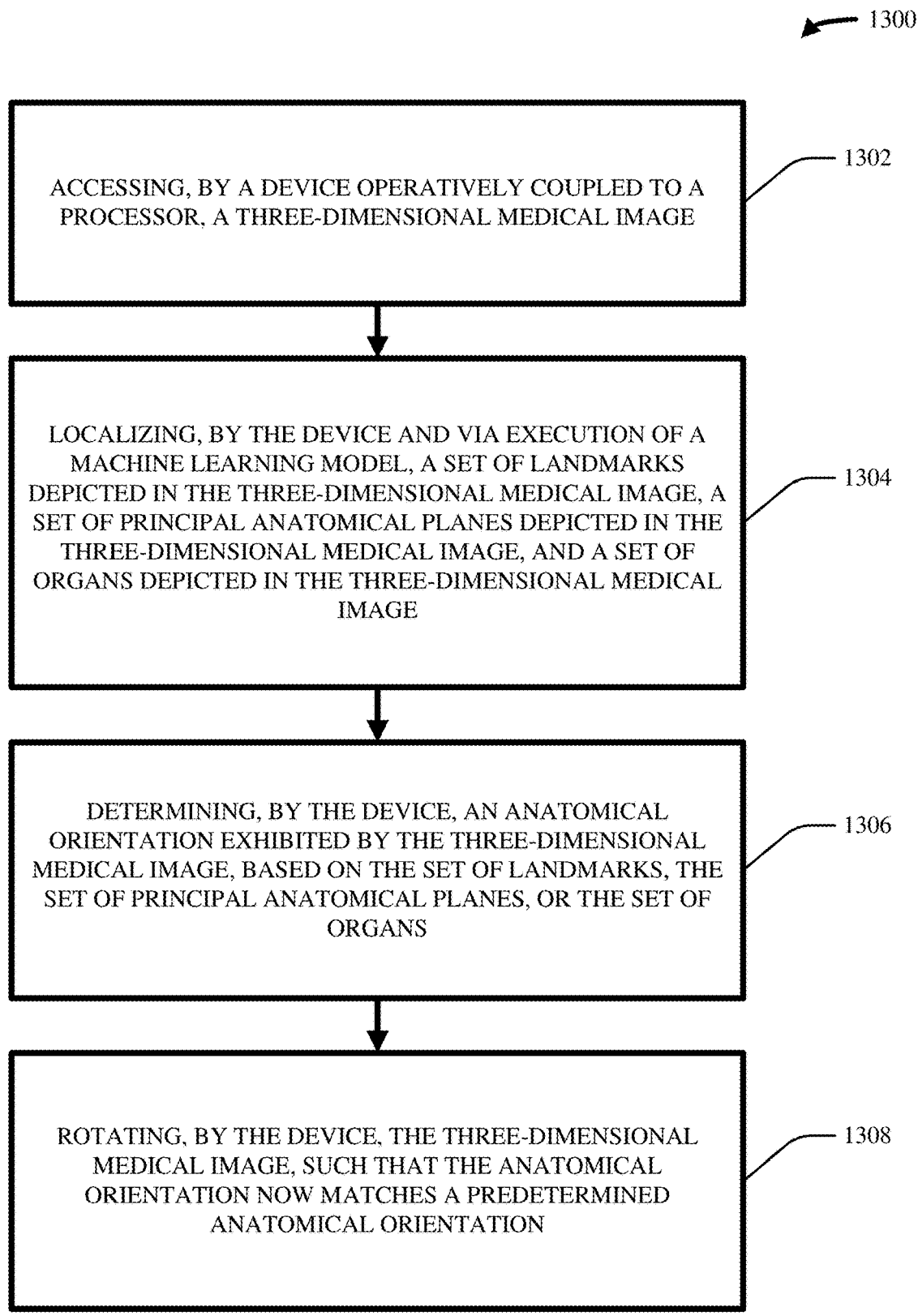
FIG. 13 illustrates a flow diagram of an example, non-limiting computer-implemented method that facilitates deep learning multi-planar reformatting for medical images in accordance with one or more embodiments described herein.

FIG. 13 illustrates a flow diagram of an example, non-limiting computer-implemented method 1300 that can facilitate deep learning multi-planar reformatting for medical images in accordance with one or more embodiments described herein. In various cases, the multi-planar reformatting system 102 can facilitate the computer-implemented method 1300.

In various embodiments, act 1302 can include accessing, by a device (e.g., via 112) operatively coupled to a processor, a three-dimensional medical image (e.g., 104).

In various aspects, act 1304 can include localizing, by the device (e.g., via 114) and via execution of a machine learning model (e.g., 302), a set of landmarks (e.g., 304) depicted in the three-dimensional medical image, a set of principal anatomical planes (e.g., 306) depicted in the three-dimensional medical image, and a set of organs (e.g., 308) depicted in the three-dimensional medical image.

In various instances, act 1306 can include determining, by the device (e.g., via 116), an anatomical orientation (e.g., 802) exhibited by the three-dimensional medical image, based on the set of landmarks, the set of principal anatomical planes, or the set of organs.

In various cases, act 1308 can include rotating, by the device (e.g., via 118), the three-dimensional medical image, such that the anatomical orientation now matches a predetermined anatomical orientation (e.g., 106).

Although not explicitly shown in FIG. 13, the computer-implemented method 1300 can further include: rendering, by the device (e.g., via 118) and on an electronic display, at least one cross-section of the three-dimensional medical image according to the predetermined anatomical orientation.

Although not explicitly shown in FIG. 13, the computer-implemented method 1300 can further include: training, by the device (e.g., via 1002), the machine learning model in supervised fashion based on a training dataset (e.g., 1004).

Although not explicitly shown in FIG. 13, the determining the anatomical orientation can include: determining, by the device (e.g., via 116), a first estimated orientation (e.g., 902) of the three-dimensional medical image based on the set of landmarks; determining, by the device (e.g., via 116), a second estimated orientation (e.g., 904) of the three-dimensional medical image based on the set of principal anatomical planes; determining, by the device (e.g., via 116), a third estimated orientation (e.g., 906) of the three-dimensional medical image based on the set of organs; and aggregating, by the device (e.g., via 116), the first estimated orientation, the second estimated orientation, and the third estimated orientation.

Although not explicitly shown in FIG. 13, the computer-implemented method 1300 can further comprise: after the rotating the three-dimensional medical image, localizing, by the device (e.g., via 114) and via execution of the machine learning model, a second set of landmarks depicted in the three-dimensional medical image that are finer than the set of landmarks (e.g., progressively finer and/or smaller landmarks depicted in a portion of the three-dimensional medical image), a second set of principal anatomical planes depicted in the three-dimensional medical image that are finer than the set of principal anatomical planes (e.g., progressively finer and/or smaller principal planes depicted in the portion of the three-dimensional medical image), and a second set of organs depicted in the three-dimensional medical image that are finer than the set of organs (e.g., progressively finer and/or smaller organs depicted in the portion of the three-dimensional medical image); and re-rotating, by the device (e.g., via 118), the three-dimensional medical image based on at least one of the second set of landmarks, the second set of principal anatomical planes, or the second set of organs.

Accordingly, various embodiments described herein include a computerized tool that can receive a medical image volume and that can utilize a deep learning technique to perform multi-planar reformatting on the medical image volume. Such a computerized tool is certainly a useful and practical application of computers.

Although the herein disclosure mainly describes various embodiments of the subject innovation as applying to image volumes (e.g., voxel arrays), this is a mere non-limiting example. In various embodiments, the herein-described teachings can be applied and/or extrapolated to any suitable images regardless of the dimensionality of such images (e.g., can be applied to pixel arrays; are not limited to voxel arrays). For example, in various aspects, the receiver component 112 can electronically receive, retrieve, and/or otherwise access a 2D medical image (e.g., a two-dimensional pixel array). In such case, the machine learning model 302 can be trained and/or otherwise configured to operate on two-dimensional input rather than three-dimensional input. Accordingly, in various instances, the detection component 114 can execute the machine learning model 302 on the 2D medical image, and the result of such execution can be a set of anatomical landmark localizations, a set of principal anatomical line (e.g., not plane) localizations, and/or a set of organ segmentations. In such case, the set of anatomical landmark localizations can indicate which pixels of the 2D medical image belong to which anatomical landmarks, the set of principal anatomical line localizations can identify the locations/positions of lines (not planes) that transect the 2D medical image in predefined ways (e.g., sagittal line, coronal line, transverse line), and/or the set of organ segmentations can indicate which pixels of the 2D medical image belong to which organs. Much as described above, the orientation component 116 can then determine a current orientation of the 2D medical image based on such output of the machine learning model 302, and the execution component 118 can rotate and/or reorient the 2D medical image accordingly.

Although the herein disclosure mainly describes various embodiments of the subject innovation as applying to medical images (e.g., X-ray images, CT images, MRI images, ultrasound images, PET images), this is a mere non-limiting example for ease of explanation. Those having ordinary skill in the art will appreciate that the herein described teachings can be applied and/or extrapolated to any suitable images for which multi-planar reformatting is desired, even if outside of a medical context.

In various instances, machine learning algorithms and/or models can be implemented in any suitable way to facilitate any suitable aspects described herein. To facilitate some of the above-described machine learning aspects of various embodiments of the subject innovation, consider the following discussion of artificial intelligence (AI). Various embodiments of the present innovation herein can employ artificial intelligence to facilitate automating one or more features of the present innovation. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) of the present innovation, components of the present innovation can examine the entirety or a subset of the data to which it is granted access and can provide for reasoning about or determine states of the system and/or environment from a set of observations as captured via events and/or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes and/or systems (e.g., support vector machines, neural networks, expert systems, Bayesian belief networks, fuzzy logic, data fusion engines, and so on) in connection with performing automatic and/or determined action in connection with the claimed subject matter. Thus, classification schemes and/or systems can be used to automatically learn and perform a number of functions, actions, and/or determinations.

A classifier can map an input attribute vector, $z=(z_1, z_2, z_3, z_4, \ldots, z_n)$, to a confidence that the input belongs to a class, as by $f(z)=confidence(class)$. Such classification can employ a probabilistic and/or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and/or probabilistic classification models providing different patterns of independence, any of which can be employed. Classification as used herein also is inclusive of statistical regression that is utilized to develop models of priority.

Those having ordinary skill in the art will appreciate that the herein disclosure describes non-limiting examples of various embodiments of the subject innovation. For ease of description and/or explanation, various portions of the herein disclosure utilize the term "each" when discussing various embodiments of the subject innovation. Those having ordinary skill in the art will appreciate that such usages of the term "each" are non-limiting examples. In other words, when the herein disclosure provides a description that is applied to "each" of some particular object and/or component, it should be understood that this is a non-limiting example of various embodiments of the subject innovation, and it should be further understood that, in various other embodiments of the subject innovation, it can be the case that such description applies to fewer than "each" of that particular object and/or component.

Figure 14:
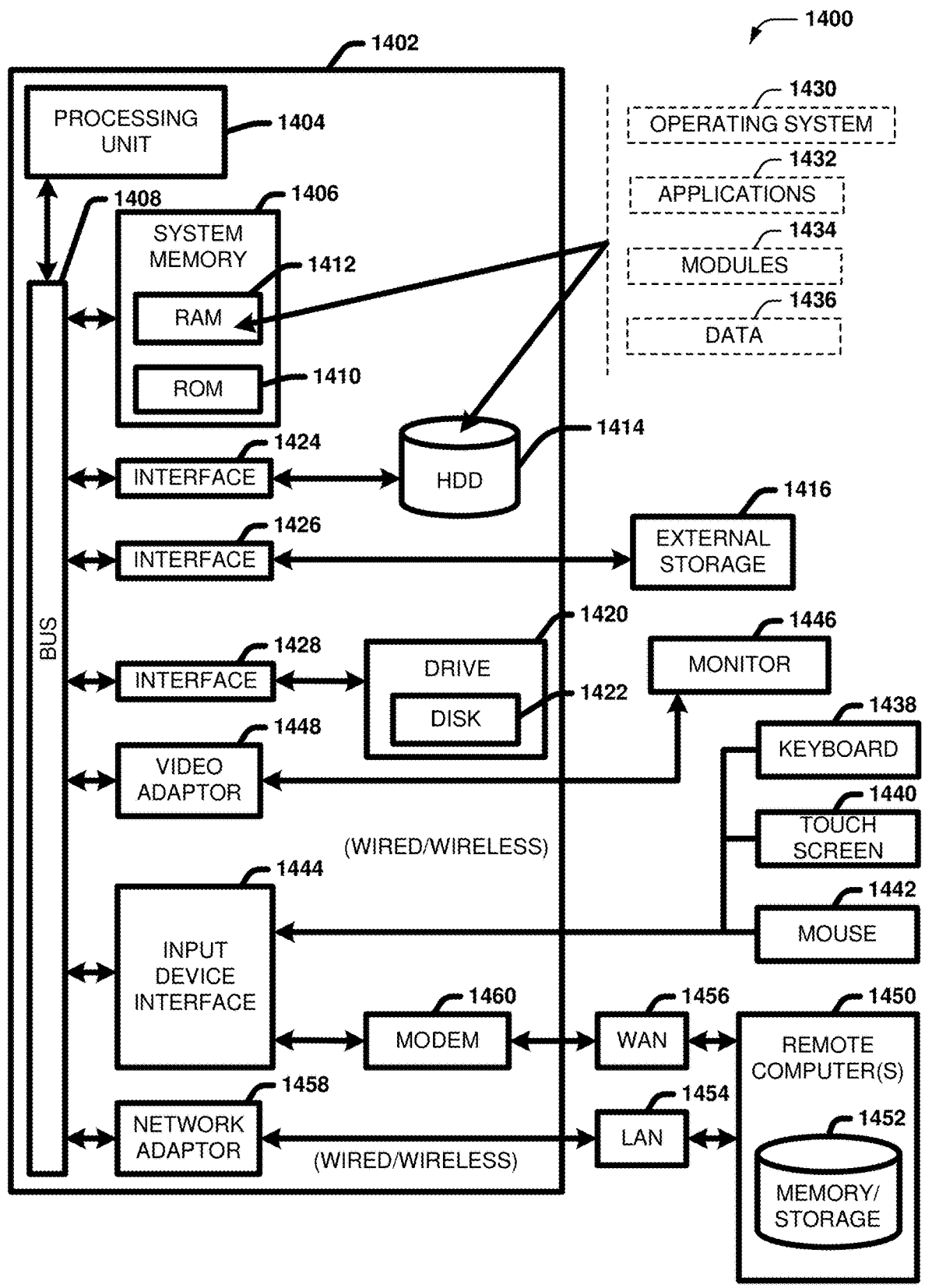
FIG. 14 illustrates a block diagram of an example, non-limiting operating environment in which one or more embodiments described herein can be facilitated.

In order to provide additional context for various embodiments described herein, FIG. 14 and the following discussion are intended to provide a brief, general description of a suitable computing environment 1400 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multi-processor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 14, the example environment 1400 for implementing various embodiments of the aspects described herein includes a computer 1402, the computer 1402 including a processing unit 1404, a system memory 1406 and a system bus 1408. The system bus 1408 couples system components including, but not limited to, the system memory 1406 to the processing unit 1404. The processing unit 1404 can be any of various commercially available processors. Dual microprocessors and other multi-processor architectures can also be employed as the processing unit 1404.

The system bus 1408 can be any of several types of bus structure that can further interconnect to a memory bus (with or without a memory controller), a peripheral bus, and a local bus using any of a variety of commercially available bus architectures. The system memory 1406 includes ROM 1410 and RAM 1412. A basic input/output system (BIOS) can be stored in a non-volatile memory such as ROM, erasable programmable read only memory (EPROM), EEPROM, which BIOS contains the basic routines that help to transfer information between elements within the computer 1402, such as during startup. The RAM 1412 can also include a high-speed RAM such as static RAM for caching data.

The computer 1402 further includes an internal hard disk drive (HDD) 1414 (e.g., EIDE, SATA), one or more external storage devices 1416 (e.g., a magnetic floppy disk drive (FDD) 1416, a memory stick or flash drive reader, a memory card reader, etc.) and a drive 1420, e.g., such as a solid state drive, an optical disk drive, which can read or write from a disk 1422, such as a CD-ROM disc, a DVD, a BD, etc. Alternatively, where a solid state drive is involved, disk 1422 would not be included, unless separate. While the internal HDD 1414 is illustrated as located within the computer 1402, the internal HDD 1414 can also be configured for external use in a suitable chassis (not shown). Additionally, while not shown in environment 1400, a solid state drive (SSD) could be used in addition to, or in place of, an HDD 1414. The HDD 1414, external storage device(s) 1416 and drive 1420 can be connected to the system bus 1408 by an HDD interface 1424, an external storage interface 1426 and a drive interface 1428, respectively. The interface 1424 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1402, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1412, including an operating system 1430, one or more application programs 1432, other program modules 1434 and program data 1436. All or portions of the operating system, applications, modules, and/or data can also be cached in the RAM 1412. The systems and methods described herein can be implemented utilizing various commercially available operating systems or combinations of operating systems.

Computer 1402 can optionally comprise emulation technologies. For example, a hypervisor (not shown) or other intermediary can emulate a hardware environment for operating system 1430, and the emulated hardware can optionally be different from the hardware illustrated in FIG. 14. In such an embodiment, operating system 1430 can comprise one virtual machine (VM) of multiple VMs hosted at computer 1402. Furthermore, operating system 1430 can provide runtime environments, such as the Java runtime environment or the .NET framework, for applications 1432. Runtime environments are consistent execution environments that allow applications 1432 to run on any operating system that includes the runtime environment. Similarly, operating system 1430 can support containers, and applications 1432 can be in the form of containers, which are lightweight, standalone, executable packages of software that include, e.g., code, runtime, system tools, system libraries and settings for an application.

Further, computer 1402 can be enable with a security module, such as a trusted processing module (TPM). For instance with a TPM, boot components hash next in time boot components, and wait for a match of results to secured values, before loading a next boot component. This process can take place at any layer in the code execution stack of computer 1402, e.g., applied at the application execution level or at the operating system (OS) kernel level, thereby enabling security at any level of code execution.

A user can enter commands and information into the computer 1402 through one or more wired/wireless input devices, e.g., a keyboard 1438, a touch screen 1440, and a pointing device, such as a mouse 1442. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1404 through an input device interface 1444 that can be coupled to the system bus 1408, but can be connected by other interfaces, such as a parallel port, an IEEE 1394 serial port, a game port, a USB port, an IR interface, a BLUETOOTH® interface, etc.

A monitor 1446 or other type of display device can be also connected to the system bus 1408 via an interface, such as a video adapter 1448. In addition to the monitor 1446, a computer typically includes other peripheral output devices (not shown), such as speakers, printers, etc.

The computer 1402 can operate in a networked environment using logical connections via wired and/or wireless communications to one or more remote computers, such as a remote computer(s) 1450. The remote computer(s) 1450 can be a workstation, a server computer, a router, a personal computer, portable computer, microprocessor-based entertainment appliance, a peer device or other common network node, and typically includes many or all of the elements described relative to the computer 1402, although, for purposes of brevity, only a memory/storage device 1452 is illustrated. The logical connections depicted include wired/wireless connectivity to a local area network (LAN) 1454 and/or larger networks, e.g., a wide area network (WAN) 1456. Such LAN and WAN networking environments are commonplace in offices and companies, and facilitate enterprise-wide computer networks, such as intranets, all of which can connect to a global communications network, e.g., the Internet.

When used in a LAN networking environment, the computer 1402 can be connected to the local network 1454 through a wired and/or wireless communication network interface or adapter 1458. The adapter 1458 can facilitate wired or wireless communication to the LAN 1454, which can also include a wireless access point (AP) disposed thereon for communicating with the adapter 1458 in a wireless mode.

When used in a WAN networking environment, the computer 1402 can include a modem 1460 or can be connected to a communications server on the WAN 1456 via other means for establishing communications over the WAN 1456, such as by way of the Internet. The modem 1460, which can be internal or external and a wired or wireless device, can be connected to the system bus 1408 via the input device interface 1444. In a networked environment, program modules depicted relative to the computer 1402 or portions thereof, can be stored in the remote memory/storage device 1452. It will be appreciated that the network connections shown are example and other means of establishing a communications link between the computers can be used.

When used in either a LAN or WAN networking environment, the computer 1402 can access cloud storage systems or other network-based storage systems in addition to, or in place of, external storage devices 1416 as described above, such as but not limited to a network virtual machine providing one or more aspects of storage or processing of information. Generally, a connection between the computer 1402 and a cloud storage system can be established over a LAN 1454 or WAN 1456 e.g., by the adapter 1458 or modem 1460, respectively. Upon connecting the computer 1402 to an associated cloud storage system, the external storage interface 1426 can, with the aid of the adapter 1458 and/or modem 1460, manage storage provided by the cloud storage system as it would other types of external storage. For instance, the external storage interface 1426 can be configured to provide access to cloud storage sources as if those sources were physically connected to the computer 1402.

The computer 1402 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Figure 15:
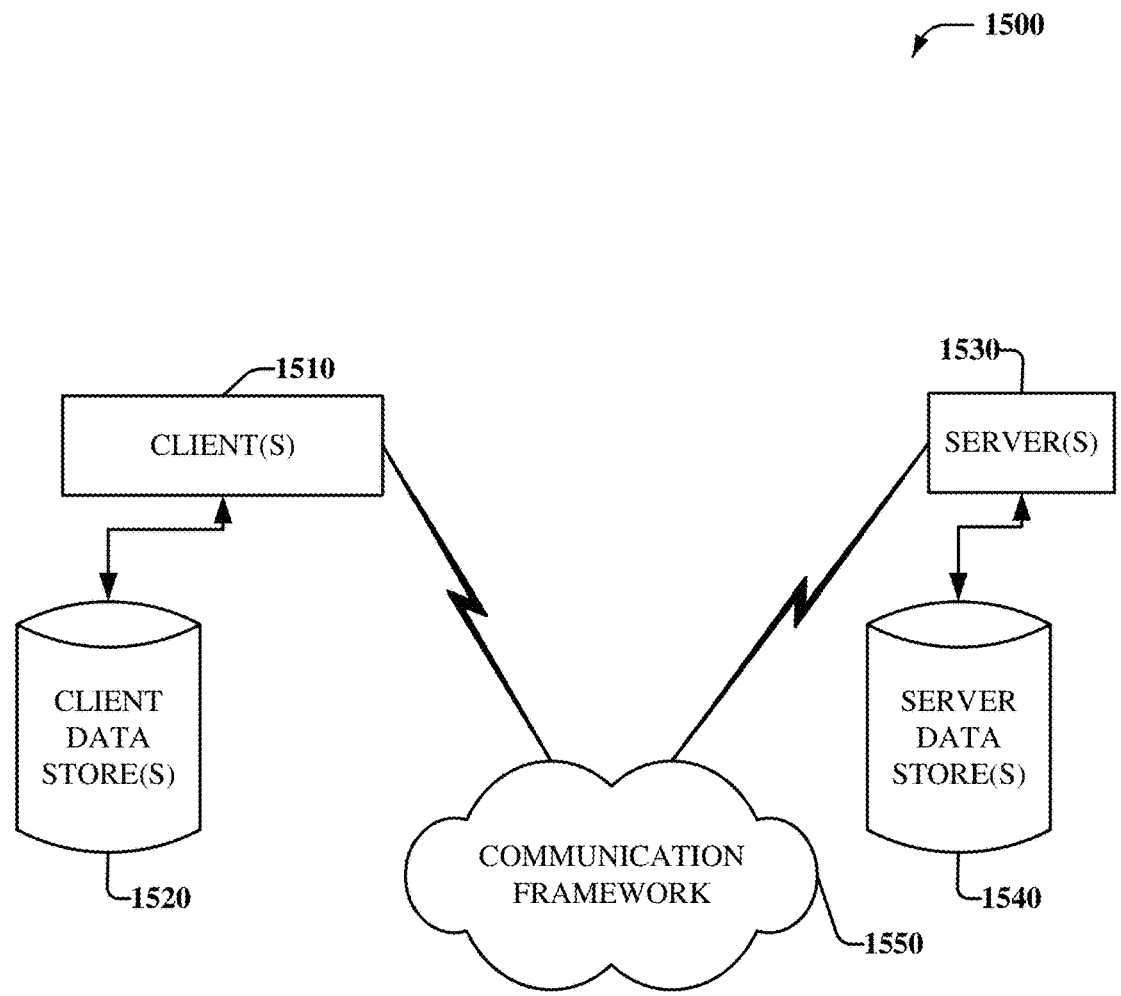
FIG. 15 illustrates an example networking environment operable to execute various implementations described herein.

FIG. 15 is a schematic block diagram of a sample computing environment 1500 with which the disclosed subject matter can interact. The sample computing environment 1500 includes one or more client(s) 1510. The client(s) 1510 can be hardware and/or software (e.g., threads, processes, computing devices). The sample computing environment 1500 also includes one or more server(s) 1530. The server(s) 1530 can also be hardware and/or software (e.g., threads, processes, computing devices). The servers 1530 can house threads to perform transformations by employing one or more embodiments as described herein, for example. One possible communication between a client 1510 and a server 1530 can be in the form of a data packet adapted to be transmitted between two or more computer processes. The sample computing environment 1500 includes a communication framework 1550 that can be employed to facilitate communications between the client(s) 1510 and the server(s) 1530. The client(s) 1510 are operably connected to one or more client data store(s) 1520 that can be employed to store information local to the client(s) 1510. Similarly, the server(s) 1530 are operably connected to one or more server data store(s) 1540 that can be employed to store information local to the servers 1530.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a standalone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on standalone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a processor that executes computer-executable components stored in a computer-readable memory, the computer-executable components comprising:
a receiver component that accesses a three-dimensional medical image;
a detection component that localizes, via execution of a machine learning model, a set of landmarks depicted in the three-dimensional medical image, a set of principal anatomical planes depicted in the three-dimensional medical image, and a set of organs depicted in the three-dimensional medical image; and
an orientation component that determines an anatomical orientation exhibited by the three-dimensional medical image, based on the set of landmarks, the set of principal anatomical planes, or the set of organs.

2. The system of claim 1, wherein the computer-executable components further comprise:
an execution component that rotates the three-dimensional medical image, such that the anatomical orientation now matches a predetermined anatomical orientation.

3. The system of claim 2, wherein the execution component renders, on an electronic display, at least one cross-section of the three-dimensional medical image according to the predetermined anatomical orientation.

4. The system of claim 2, wherein, after the execution component rotates the three-dimensional medical image, the detection component localizes, via execution of the machine learning model, a second set of landmarks depicted in the three-dimensional medical image that are finer than the set of landmarks, a second set of principal anatomical planes depicted in the three-dimensional medical image that are finer than the set of principal anatomical planes, and a second set of organs depicted in the three-dimensional medical image that are finer than the set of organs, and wherein the execution component re-rotates the three-dimensional medical image based on at least one of the second set of landmarks, the second set of principal anatomical planes, or the second set of organs.

5. The system of claim 1, wherein the machine learning model is a deep learning neural network, wherein the machine learning model receives as input the three-dimensional medical image, and wherein the machine learning model localizes as output the set of landmarks, the set of principal anatomical planes, and the set of organs.

6. The system of claim 1, wherein the computer-executable components further comprise:
a training component that trains the machine learning model in supervised fashion based on a training dataset.

7. The system of claim 6, wherein the training component implements a loss function that is based on a graph of landmarks localized by the machine learning model.

8. The system of claim 1, wherein the orientation component determines a first estimated orientation of the three-dimensional medical image based on the set of landmarks, wherein the orientation component determines a second estimated orientation of the three-dimensional medical image based on the set of principal anatomical planes, wherein the orientation component determines a third estimated orientation of the three-dimensional medical image based on the set of organs, and wherein the orientation component determines the anatomical orientation by aggregating one or more of the first estimated orientation, the second estimated orientation, and the third estimated orientation.

9. A computer-implemented method, comprising:
accessing, by a device operatively coupled to a processor, a three-dimensional medical image;
localizing, by the device and via execution of a machine learning model, a set of landmarks depicted in the three-dimensional medical image, a set of principal anatomical planes depicted in the three-dimensional medical image, and a set of organs depicted in the three-dimensional medical image; and
determining, by the device, an anatomical orientation exhibited by the three-dimensional medical image, based on the set of landmarks, the set of principal anatomical planes, or the set of organs.

10. The computer-implemented method of claim 9, further comprising:
rotating, by the device, the three-dimensional medical image, such that the anatomical orientation now matches a predetermined anatomical orientation.

11. The computer-implemented method of claim 10, further comprising:
rendering, by the device and on an electronic display, at least one cross-section of the three-dimensional medical image according to the predetermined anatomical orientation.

12. The computer-implemented method of claim 10, further comprising:
after the rotating the three-dimensional medical image, localizing, by the device and via execution of the machine learning model, a second set of landmarks depicted in the three-dimensional medical image that are finer than the set of landmarks, a second set of principal anatomical planes depicted in the three-dimensional medical image that are finer than the set of principal anatomical planes, and a second set of organs depicted in the three-dimensional medical image that are finer than the set of organs; and
re-rotating, by the device, the three-dimensional medical image based on at least one of the second set of landmarks, the second set of principal anatomical planes, or the second set of organs.

13. The computer-implemented method of claim 9, wherein the machine learning model is a deep learning neural network, wherein the machine learning model receives as input the three-dimensional medical image, and wherein the machine learning model localizes as output the set of landmarks, the set of principal anatomical planes, and the set of organs.

14. The computer-implemented method of claim 9, further comprising:
   training, by the device, the machine learning model in supervised fashion based on a training dataset.

15. The computer-implemented method of claim 14, wherein the training implements a loss function that is based on a graph of landmarks localized by the machine learning model.

16. The computer-implemented method of claim 9, wherein the determining the anatomical orientation includes:
   determining, by the device, a first estimated orientation of the three-dimensional medical image based on the set of landmarks;
   determining, by the device, a second estimated orientation of the three-dimensional medical image based on the set of principal anatomical planes;
   determining, by the device, a third estimated orientation of the three-dimensional medical image based on the set of organs; and
   aggregating, by the device, one or more of the first estimated orientation, the second estimated orientation, and the third estimated orientation.

\* \* \* \* \*